US012275953B2

(12) United States Patent
Lin et al.

(10) Patent No.: US 12,275,953 B2
(45) Date of Patent: Apr. 15, 2025

(54) METHODS FOR SCREENING HOST CELLS EXPRESSING TARGET PROTEINS

(71) Applicant: Industrial Technology Research Institute, Hsinchu (TW)

(72) Inventors: Yen-Ju Lin, Taichung (TW); Mei-Wei Lin, Zhubei (TW); Min-Yuan Chou, Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 149 days.

(21) Appl. No.: 17/564,729

(22) Filed: Dec. 29, 2021

(65) Prior Publication Data

US 2022/0228110 A1     Jul. 21, 2022

Related U.S. Application Data

(60) Provisional application No. 63/131,492, filed on Dec. 29, 2020.

(51) Int. Cl.
*C12N 5/00* (2006.01)
*C07K 14/47* (2006.01)
*C12N 15/85* (2006.01)
*G01N 33/50* (2006.01)

(52) U.S. Cl.
CPC ........ *C12N 5/0081* (2013.01); *C07K 14/4717* (2013.01); *C12N 15/85* (2013.01); *G01N 33/5014* (2013.01)

(58) Field of Classification Search
None
See application file for complete search history.

(56) References Cited

U.S. PATENT DOCUMENTS 10,206,987 B2    2/2019 Lee et al.

FOREIGN PATENT DOCUMENTS

| CN | 105349579 A | 2/2016 |
| CN | 109803642 A | 5/2019 |
| KR | 20090129234 | * 12/2009 |

OTHER PUBLICATIONS

Mumbauer et al., "Ferritin heavy chain protects the developing wing from reactive oxygen species and ferroptosis," PLOS Genetics, Sep. 30, 2019, pp. 1-18.
Taiwanese Office Action and Search Report dated Aug. 29, 2023 for Application No. 110149400.
Feng et al., "Unsolved mysteries: How does lipid peroxidation cause ferroptosis?", PLOS Biology, May 24, 2018, pp. 1-15.
Wang et al., "HSF1 functions as a key defender against palmitic acid-induced ferroptosis in cardiomyocytes", Journal of Molecular and Cellular Cardiology, 2021, vol. 150, pp. 65-76.

* cited by examiner

*Primary Examiner* — Anoop K Singh
(74) *Attorney, Agent, or Firm* — Birch, Stewart, Kolasch & Birch, LLP

(57) ABSTRACT

A method for screening host cells expressing a target protein is provided. The method includes the following steps: providing an expression vector, the expression vector including a promoter, a gene encoding a target protein and an FTH1 gene; transfecting the host cells with the expression vector; culturing the host cells in a medium; and adding iron ions to the medium, and screening the surviving host cells to obtain the host cells expressing the target protein. An expression vector and a method for establishing a cell line stably expressing an exogenous recombinant gene are also provided.

10 Claims, 23 Drawing Sheets

Specification includes a Sequence Listing.

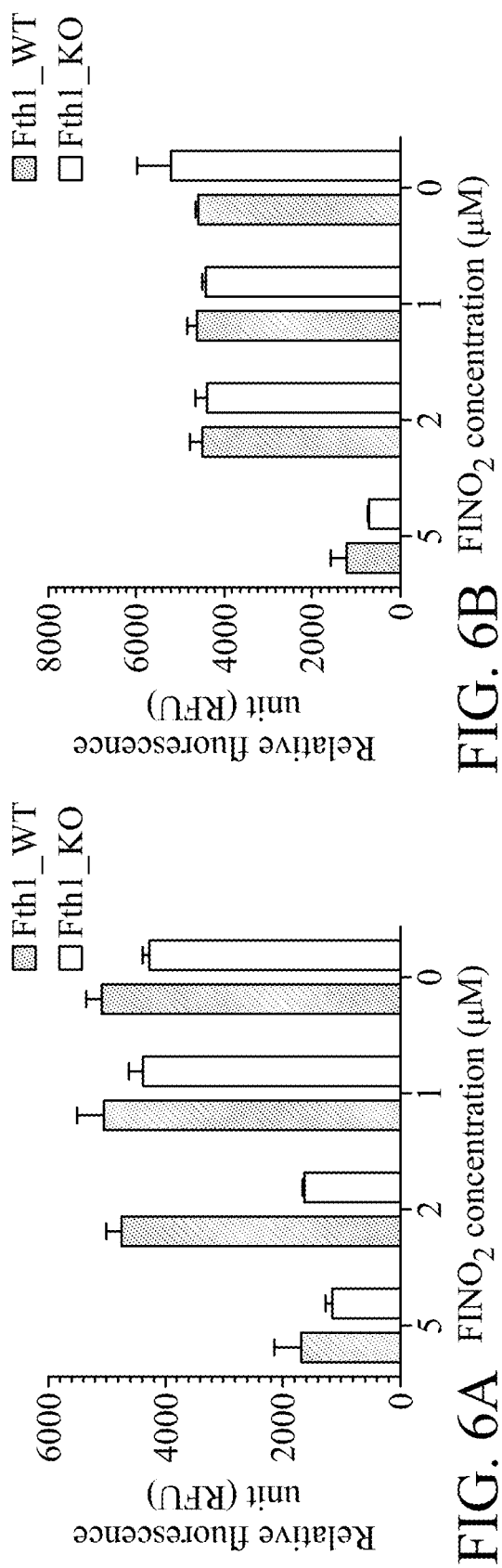
FIG. 6A
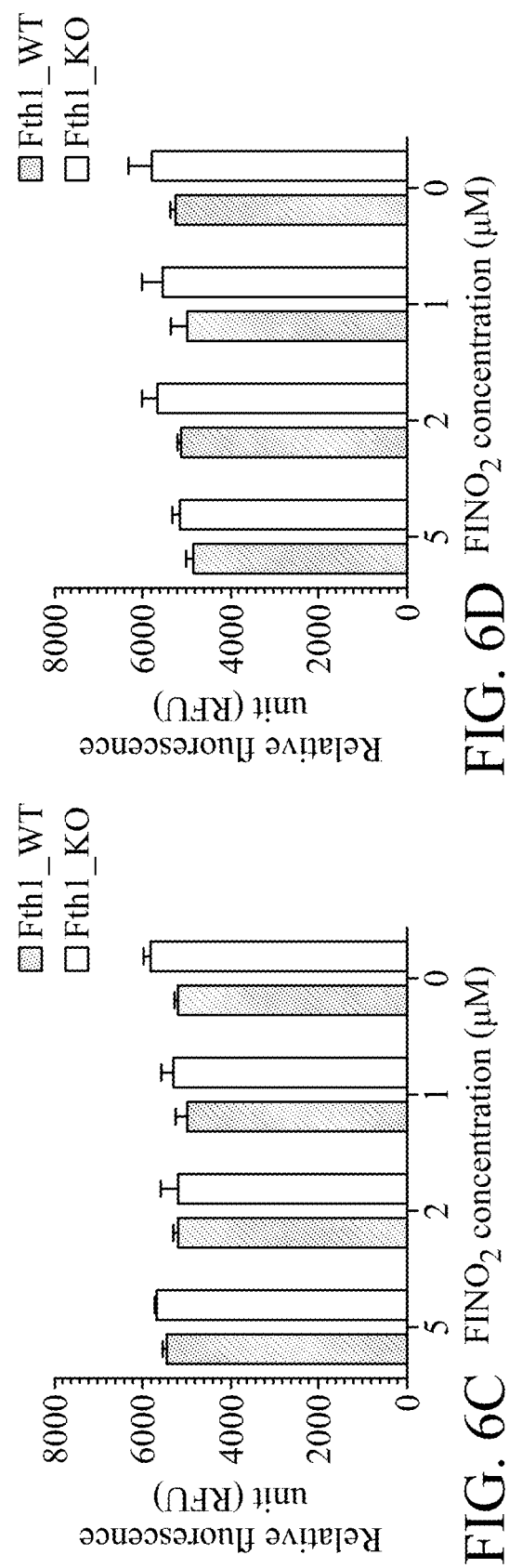
FIG. 6B
FIG. 6C
FIG. 6D

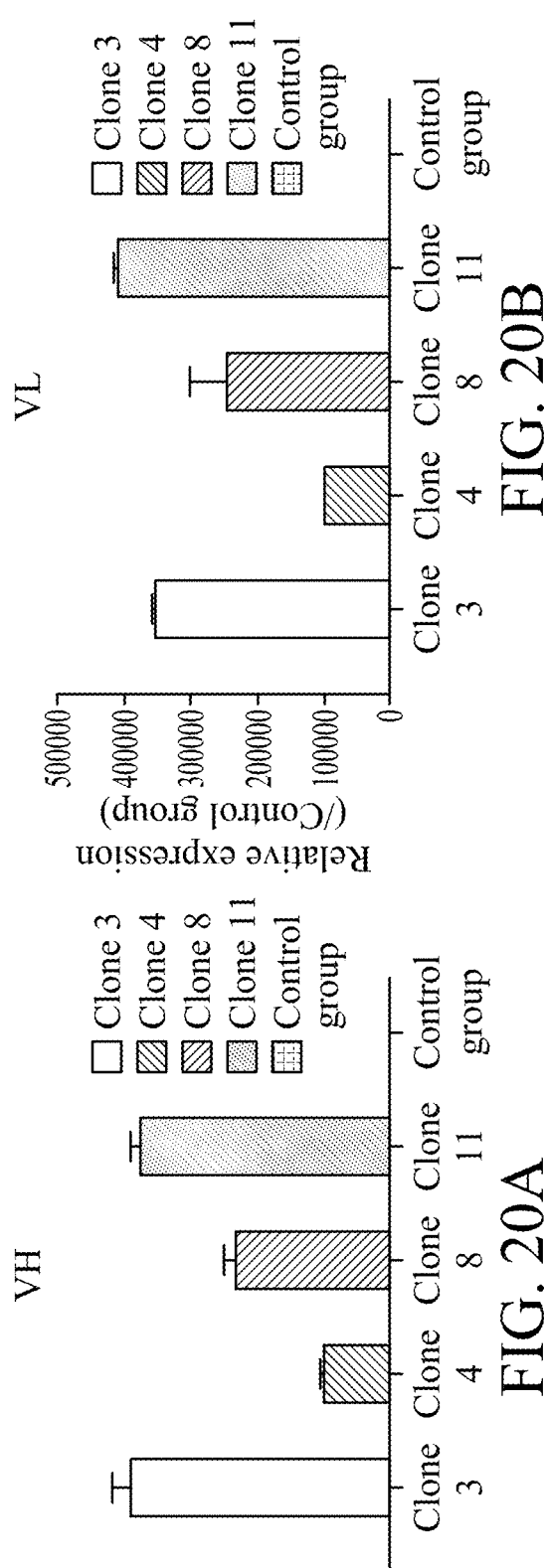
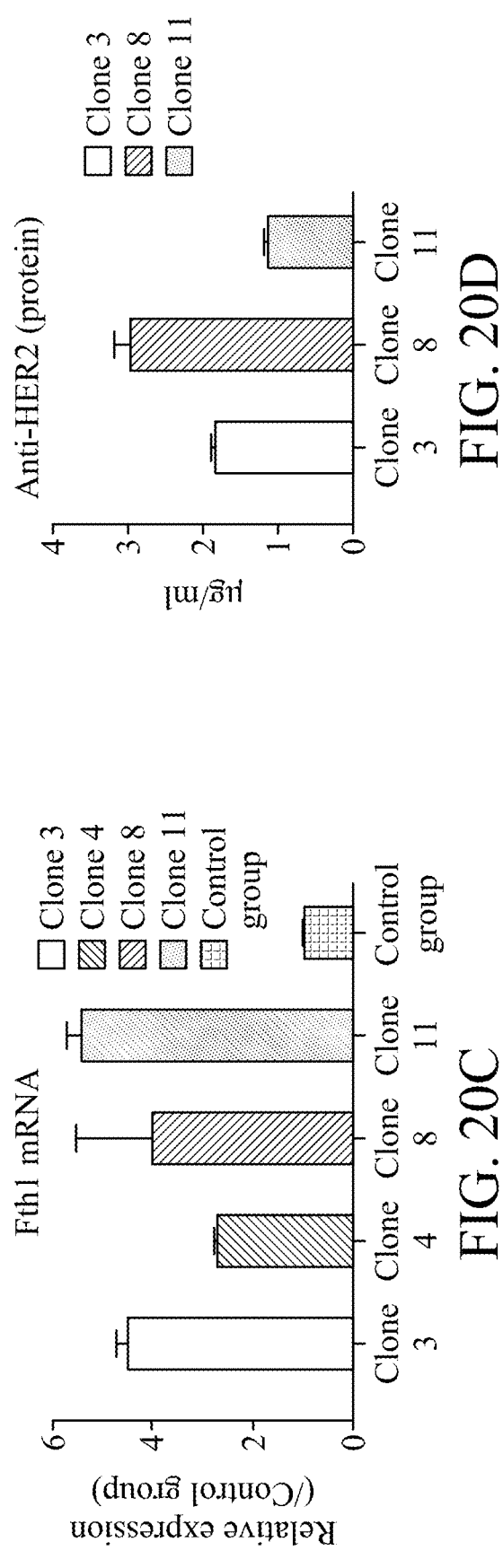
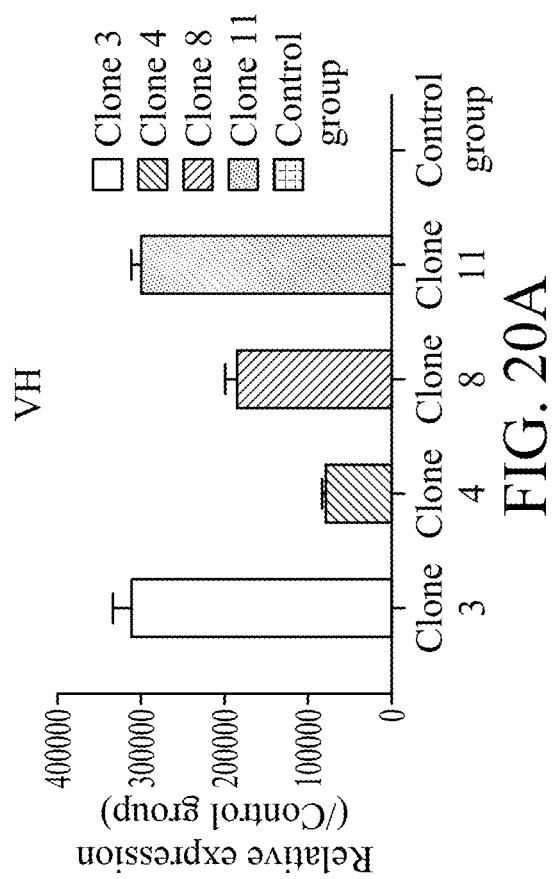
FIG. 20A, FIG. 20B, FIG. 20C, FIG. 20D

METHODS FOR SCREENING HOST CELLS EXPRESSING TARGET PROTEINS

CROSS REFERENCE TO RELATED APPLICATIONS

This application claims the benefit of U.S. Provisional Application No. 63/131,492, filed Dec. 29, 2020, the entirety of which is incorporated by reference herein.

INCORPORATION BY REFERENCE OF SEQUENCE LISTING

A sequence listing submitted as a text file via EFS-Web is incorporated herein by reference. The text file containing the sequence listing is named "9044B-A27922_US_Seq_Listing.txt"; its date of creation was Dec. 28, 2021; and its size is 17,676 bytes.

BACKGROUND

Technical Field

The present disclosure relates to the construction of an expression vector using FTH1 (Ferritin Heavy Chain 1) gene, and the application of FTH1 gene to a method for screening host cells expressing a target protein, a method for establishing a stable cell line, and a method for preparing a recombinant protein.

Description of the Related Art

To improve the quality of pharmaceutical-grade recombinant protein drugs, in addition to the optimization of the culture environment of cell-line, and the improvement of purification and process technology, establishing a high-efficiency screening system for a stable cell line to culture high-performance production cell lines is also an important key.

Generally, mammalian cells are ideal host cells for the production of complex recombinant protein drugs, mainly because their modifications carried out after translation are compatible with humans in terms of function and pharmacokinetics. In order to produce stable mammalian cell lines expressing the heterologous gene of interest, the heterologous gene, along with a selectable marker gene (e.g., neomycin phosphotransferase), is often introduced into the cell line used by transfection, including the expression of the heterologous gene and the selectable marker gene by a single vector or by co-transfected different vectors. In addition, 2 to 3 days after transfection, if the cells are subsequently cultured in a medium containing the selective agent (e.g., medium containing G418 when the neomycin phosphotransferase gene is used) for several weeks, then the drug-resistant cells can be isolated, and the performance of their gene products can be further investigated. However, since the obtained cell populations have different proportions of heterologous gene expression, in order to identify a pure cell line that highly expresses the heterologous gene of interest, a large number of pure cell lines need to be examined and tested, which is time-consuming, labor-intensive and quite expensive.

Gene amplification is quite common in animal cell culture for the production of recombinant protein drugs, and it improves the initially relatively low productivity of many mammalian cell lines. Widely used amplification techniques, such as a gene amplification system based on dihydrofolate reductase (DHFR), is often used in DHFR-deficient Chinese hamster ovary (CHO) cells. This technique allows the transfection of DHFR-deficient CHO cells with a vector carrying genes encoding DHFR and the protein of interest, followed by screening of transfected cells in a medium without glycine, hypoxanthine and thymidine, and the high-productivity cell line amplification can be achieved through the increasing addition of methotrexate (MTX), an inhibitor of dihydrofolate reductase. However, in order to establish stable cell lines, subsequent screening of the obtained high-productivity cells is also highly labor-intensive and time-consuming.

In view of the foregoing, the development of a novel cell line screening system to establish a high-efficiency stable cell line is still one of the main research goals of the pharmaceutical industry.

SUMMARY

In accordance with some embodiments of the present disclosure, a method for screening host cells expressing a target protein is provided. The method includes the following steps: providing an expression vector, the expression vector including a promoter, a gene encoding a target protein and an FTH1 gene; transfecting the host cells with the expression vector; culturing the host cells in a medium; and adding iron ions to the medium, and screening the surviving host cells to obtain the host cells expressing the target protein.

In accordance with some embodiments of the present disclosure, a method for establishing a stable cell line is provided. The method includes the following steps: providing an expression vector, the expression vector including a promoter, a gene encoding a target protein and an FTH1 gene; transfecting host cells with the expression vector; culturing the host cells in a medium; and adding iron ions to the medium, and continuously culturing the host cells in the medium containing iron ions for a period of time to screen and obtain a cell line that stably expresses the gene encoding the target protein.

In accordance with some embodiments of the present disclosure, an expression vector is provided. The expression vector includes a promoter, a gene encoding a target protein and an FTH1 gene, and the promoter is linked to the gene encoding the target protein and the FTH1 gene.

In accordance with some embodiments of the present disclosure, a eukaryotic host cell is provided, which is formed by transfection of the aforementioned expression vector.

In accordance with some embodiments of the present disclosure, a method for preparing a recombinant protein is provided. The method includes the following steps: culturing the aforementioned eukaryotic host cell in a medium; and isolating the recombinant protein from the medium.

In accordance with some embodiments of the present disclosure, a method for establishing a cell line stably expressing an exogenous recombinant gene is provided, in which an FTH1 gene is used as a selection marker to screen out a host cell with an exogenous recombinant gene.

In order to make the features or advantages of the present disclosure clear and easy to understand, a detailed description is given in the following embodiments with reference to the accompanying drawings.

BRIEF DESCRIPTION OF THE DRAWINGS

FIGS. 6A to 6D show analysis results of the effects of the CHOK1 cell lines Fth1_WT and Fth1_KO in the screening formulations with different compositions on iron ion-induced ferroptosis in accordance with some embodiments of the present disclosure.

FIG. 20A shows analysis results of the mRNA expression level of the heavy chain (VH) of Anti-HER2 IgG1(h4D5) antibody obtained from the CHOK1 cell lines transfected with the expression vector pcDNA3.1-CMV-GOI1-furin-p2A-GOI2-IRES-cgFth1 in accordance with some embodiments of the present disclosure.

FIG. 20B shows analysis results of the mRNA expression level of the light chain (VL) of Anti-HER2 IgG1(h4D5) antibody obtained from the CHOK1 cell lines transfected with the expression vector pcDNA3.1-CMV-GOI1-furin-p2A-GOI2-IRES-cgFth1 in accordance with some embodiments of the present disclosure.

FIG. 20C shows analysis results of the mRNA expression of FTH1 gene of the CHOK1 cell lines transfected with the expression vector pcDNA3.1-CMV-GOI1-furin-p2A-GOI2-IRES-cgFth1 in accordance with some embodiments of the present disclosure.

FIG. 20D shows ELISA analysis results of the expression level of Anti-HER2 IgG1(h4D5) antibody obtained from the CHOK1 cell line transfected with the expression vector pcDNA3.1-CMV-GOI1-furin-p2A-GOI2-IRES-cgFth1 in accordance with some embodiments of the present disclosure.

DETAILED DESCRIPTION

Figure 1A:
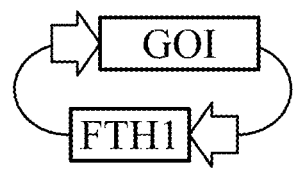
FIGS. 1A to 1C show schematic diagrams of the constructed expression vectors in accordance with some embodiments of the present disclosure.

The expression vector, the method for screening host cells expressing a target protein, the method for establishing a stable cell line, and the method for preparing a recombinant protein of the present disclosure are described in detail in the following description. It should be understood that in the following detailed description, for purposes of explanation, numerous specific details and embodiments are set forth in order to provide a thorough understanding of the present disclosure. The specific elements and configurations described in the following detailed description are set forth in order to clearly describe the present disclosure. It will be apparent that the exemplary embodiments set forth herein are used merely for the purpose of illustration and not the limitation of the present disclosure.

In the following description, the terms "about" and "substantially" typically mean +/−10% of the stated value, or typically +/−5% of the stated value, or typically +/−3% of the stated value, or typically +/−2% of the stated value, or typically +/−1% of the stated value or typically +/−0.5% of the stated value. The stated value of the present disclosure is an approximate value. When there is no specific description, the stated value includes the meaning of "about" and "substantially". In addition, the term "between the first value and the second value" or "in a range from the first value to the second value" means that the range includes the first value, the second value, and other values in between.

Unless defined otherwise, all technical and scientific terms used herein have the same meaning as commonly understood by one of ordinary skill in the art to which this disclosure belongs. It should be appreciated that, in each case, the term, which is defined in a commonly used dictionary, should be interpreted as having a meaning that conforms to the relative skills of the present disclosure and the background or the context of the present disclosure, and should not be interpreted in an idealized or overly formal manner unless so defined.

The term "FTH1 gene" refers to the ferritin heavy chain 1 (Ferritin Heavy Chain 1) gene, which encodes the ferritin heavy chain, which is a ferroxidase enzyme. FTH1 gene is involved in the regulation of iron metabolism in cells, and plays an important role in iron-dependent cell death mechanism (ferroptosis). Ferritin is the main protein used to store iron ions in prokaryotes and eukaryotes. The alteration in the composition of ferritin subunits may affect the absorption rate and the release rate of irons in different tissues. The main function of ferritin is to store irons in a soluble and non-toxic state. The deficiency of ferritin is associated with a variety of neurodegenerative diseases.

The term "ferroptosis" refers to a form of cell death involving the production of reactive oxidative substances mediated by irons and resulting in lipid peroxidation. The term "ferroptosis inducer" refers to an agent that induces, promotes or activates ferroptosis.

In accordance with the embodiments of the present disclosure, the "target gene (gene of interest)" contained in the expression vector includes a nucleotide sequence of any length encoding the target product. The "gene product" or "product of interest" is usually a protein, polypeptide, peptide, or a fragment or derivative thereof. However, the "gene product" or "product of interest" may also include RNA or antisense RNA. The target gene can exist in its full-length, shortened form, or exist in a form of fusion gene or labeled gene. The gene of interest may be genomic DNA, cDNA or an equivalent fusion fragment. The gene of interest may be a native gene sequence, or a mutated or modified sequence. The modification may include codon optimization and humanization for a particular host cell.

The term "nucleotide sequence" or "nucleic acid sequence" refers to oligonucleotides, nucleotides, polynucleotides and fragments thereof, as well as DNA or RNA of genomic or synthetic origin, which can exist in a single-stranded or double-stranded form. Nucleotides may be deoxyribonucleotides, ribonucleotides, or modified nucleotides. Nucleosides consist of purine (adenine (A) or guanine (G) or their derivatives) or pyrimidine (thymine (T), cytosine (C) or uracil (U) or their derivatives) bases and sugars bonds. The four nucleoside units (or bases) in DNA are called deoxyadenosine, deoxyguanosine, deoxythymidine and deoxycytidine. The four nucleoside units (or bases) in RNA are called adenosine, guanosine, uridine and cytidine. Nucleotides are phosphate esters of nucleosides.

The term "encode" refers to the properties or functions of a specific sequence of nucleotides in nucleic acids, such as genes in chromosomes or mRNAs, that act as substrates for the synthesis of other polymers and macromolecules in organisms, for example, rRNA, tRNA, mRNA, other RNA molecules, cDNA or polypeptides. Therefore, if a protein is produced in a cell or other biological system by mRNA transcription and subsequent translation, it is called a "gene-encoded protein".

The term "host cell" refers to a cell into which exogenous nucleic acid is introduced, including the progeny of such cells. Host cells include "transformants" and "transformed cells", which include the originally transformed cell and progeny derived therefrom, regardless of the number of passages. The nucleic acid content of the progeny may not be identical to the parental cell, and may contain mutations. In accordance with the embodiments of the present disclosure, host cells include mutant progeny that have the same function or biological activity as screened or selected in the originally transformed cell.

The term "vector" refers to a nucleic acid molecule capable of propagating another nucleic acid to which it is linked. In accordance with the embodiments of the present disclosure, the vector includes a vector that is an autonomously replicating nucleic acid construct, as well as a vector that is incorporated into the genome of the host cell into which it is introduced. Certain vectors are capable of indicating the expression of nucleic acids to which they are operably linked, and such vectors are referred to herein as "expression vectors".

The term "transfect" refers to the delivery of nucleic acids, proteins, or other macromolecules to a target cell for the purpose of expressing the nucleic acid, protein, or other macromolecules within the cell or rendering it biologically functional.

The term "culture" refers to the in vitro proliferation of cells or organisms in or on various types of media. It should be understood that the progeny of cells grown in culture may not be completely identical (morphologically, genetically, or phenotypically) to the parent.

The term "promoter" or "promoter region" refers to a nucleic acid sequence located upstream (5' end) of an expressed nucleic acid sequence and controls the expression of the sequence by providing the recognition and binding sites for RNA polymerase. The promoter region may contain other recognition and binding sites of other factors involved in regulation of gene transcription. Promoters can control the transcription of prokaryotic or eukaryotic genes. Furthermore, a promoter can be an inducible promoter and can initiate transcription in response to an inducer, or can be a constitutive promoter where transcription is not under the control of an inducer. In the absence of the inducer, the gene under the control of the inducible promoter is not expressed or is expressed only slightly, whereas in the presence of the inducer, the gene initiates transcription or increases the amount of transcription, which is generally regulated by the binding of specific transcription factors.

The term "protein" can be used interchangeably with the terms "peptide" and "polypeptide". The term "recombinant protein" refers to a protein produced by recombinant DNA techniques, in which the DNA encoding the expressed protein or RNA is typically inserted into an appropriate expression vector, and the expression vector can be used to transfect host cells to produce exogenous protein or RNA. Proteins or polypeptides of biopharmaceutical importance, for example, may include antibodies, enzymes, cytokines, lymphokines, receptors and derivatives or fragments thereof, but they are not limited thereto.

The term "antibody" is used herein in the broadest sense and encompasses a variety of antibody structures, e.g., which includes monoclonal antibodies, polyclonal antibodies, multispecific antibodies (e.g., bispecific antibodies) or antibody fragments, but is not limited thereto. The term "antibody fragment" refers to a molecule other than an intact antibody that includes a portion of an intact antibody, and the antibody fragment binds to the same antigen as the intact antibody. Antibody fragments may include Fv, Fab, Fab', Fab'-SH, F(ab')$_2$; diabodies; linear antibodies; single-chain antibody molecules (e.g., scFv); and multispecific antibodies formed of antibody fragments, but they are not limited thereto.

In accordance with the embodiments of the present disclosure, several genes with high potential to enhance the performance or productivity of specific cell lines are identified, from the regulatory strategy of key cell biosynthesis pathway genes, through the analysis of biological information and functional genomics. It was found that FTH1 gene (X11 gene) is highly expressed when cells produce exogenous recombinant proteins. FTH1 gene is mainly involved in the metabolic regulation of iron ions in cells, and plays an important role in the iron-dependent cell death mechanism (ferroptosis).

Embodiments of the present disclosure have verified the relevance of FTH1 gene regulation and induction of ferroptosis in cells, and further confirmed that overexpression of FTH1 gene can significantly improve the tolerance of cell lines to the induced ferroptosis under the action of excessive iron ions addition or ferroptosis inducers. In the embodiments of the present disclosure, expression vectors and formulations of the medium are developed based on the aforementioned characteristics, so as to construct a high-efficiency cell line screening system. In this way, a cell line that can stably express exogenous recombinant genes can be established and the expression of exogenous genes in the cell line is promoted to achieve the effect of improving the yield of recombinant protein drugs.

In accordance with the embodiment of the present disclosure, a method for screening hosts cell expressing a target protein is provided. The method includes the following steps: (a) providing an expression vector, the expression vector including a promoter, a gene encoding a target protein and an FTH1 gene; (b) transfecting host cells with the expression vector; (c) culturing the host cells in a medium; and (d) adding iron ions to the medium, and screening the surviving host cells to obtain host cells expressing the target protein.

Figure 1B:
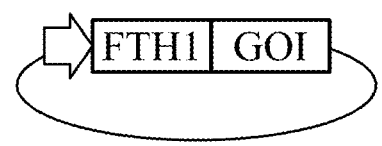
Figure 1C:
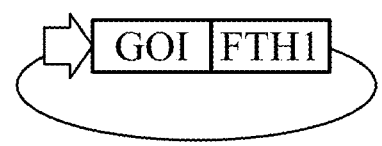

The expression vector can be designed and constructed by the techniques known in the art. In the expression vector, the promoter is linked with the gene encoding the target protein and the FTH1 gene. Specifically, as shown in FIG. 1A, in accordance with some embodiments, the gene encoding the target protein (indicated by GOI) and the FTH1 gene can be driven by different promoters (indicated by arrows). That is, the gene encoding the target protein can be driven by one promoter, and the FTH1 gene can be driven by another promoter, and the type of promoter that drives the gene encoding the target protein can be different from the type of promoter that drives the FTH1 gene. In accordance with some other embodiments, as shown in FIG. 1B and FIG. 1C, the gene encoding the target protein (indicated by GOI) and the FTH1 gene can be driven by the same promoter. As shown in FIG. 1B, in accordance with some embodiments, the gene encoding the target protein is located downstream of the FTH1 gene. As shown in FIG. 1C, in accordance with some embodiments, the gene encoding the target protein is located upstream of the FTH1 gene.

In accordance with some embodiments, the promoter driving the gene encoding the target protein or the FTH1 gene may include a CMV promoter, a SV40 promoter, an EF1α promoter or another suitable promoter, but it is not limited thereto. In accordance with some embodiments, the expression vector may further include an internal ribosome entry site (IRES) located between the gene encoding the target protein and the FTH1 gene.

The expression vector may include a nucleotide sequence of any length that encodes a target protein. In accordance with some embodiments, the target protein may include a recombinant protein, but it is not limited thereto. In accordance with some embodiments, the recombinant protein may include an antibody, but it is not limited thereto. In accordance with different embodiments, any suitable target protein can be selected for the design of the expression vector according to needs.

Furthermore, FTH1 gene is involved in the metabolic regulation of iron ions in cells, and plays an important role in the ferroptosis mechanism. The similarity of FTH1 gene among different species is high. For example, the alignment result of the amino acid sequences of FTH1 gene of human (*Homo sapiens*), mouse (*Mus musculus*) and Chinese hamster (*Cricetulus griseus*) shows that the amino acid sequences have more than 90% of similarity. In accordance with some embodiments, the amino acid sequence encoded by the FTH1 gene has at least 85%, for example, 86%, 87%, 88%, 89%, 90%, 91%, 92%, 93%, 94%, 95%, 96%, 97%, 98%, or 99%, of similarity with the sequence shown in any one of SEQ ID NOs: 1 to 3, but it is not limited thereto. In accordance with some embodiments, the FTH1 gene is an FTH1 gene derived from Chinese hamster, which encodes the amino acid sequence of SEQ ID NO: 1. In accordance with some embodiments, the FTH1 gene is an FTH1 gene derived from mouse, which encodes the amino acid sequence of SEQ ID NO: 2. In accordance with some embodiments, the FTH1 gene is an FTH1 gene derived from human, which encodes the amino acid sequence of SEQ ID NO: 3.

The transfection of host cell can be carried out by the techniques known in the art. For example, the genetic information carried by the expression vector can be introduced into the host cell by chemical transfection (e.g., liposome transfection or calcium phosphate transfection), viral transfection, electrotransfection, or other suitable methods. In accordance with some embodiments, the host cells may include, but are not limited to, CHO cells, HEK293 cells, Hela cells, VERO cells, NSO cells, or other suitable cell lines.

In accordance with some embodiments, the host cells can be first cultured in a suitable medium for a period of time, and then the host cells can be transfected with an expression vector. For example, in accordance with some embodiments, the host cells can be cultured in the medium for about 12 hours to about 36 hours, e.g., about 16 hours, about 20 hours, about 24 hours, about 28 hours, or about 32 hours, before transfection.

Figure 2:
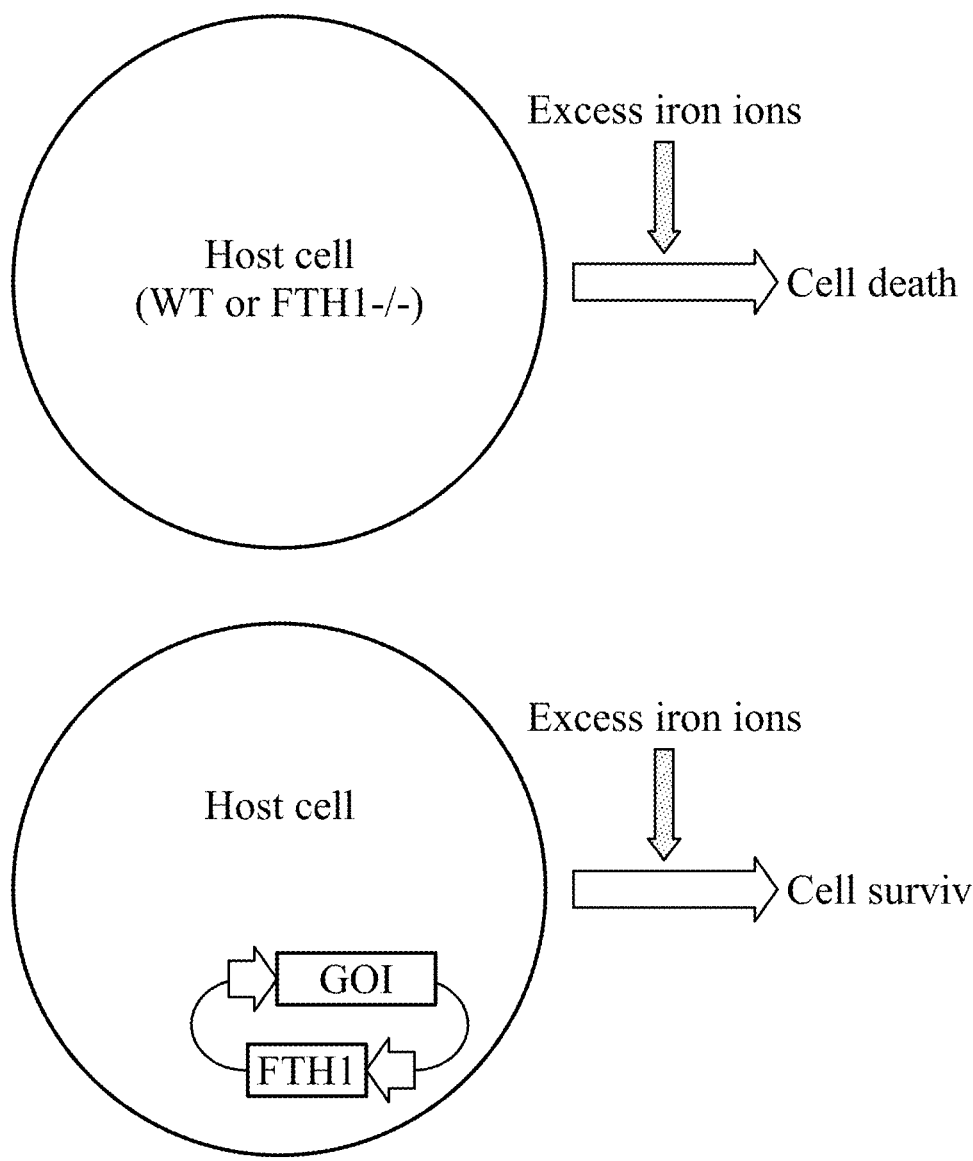
FIG. 2 shows a mechanism of cell line screening system in accordance with some embodiments of the present disclosure.

In accordance with some embodiments, after the transfection, iron ions are added to the medium to increase the iron ion concentration in the medium to induce ferroptosis, so that host cells expressing the target protein can be obtained by screening. For the detailed screening mechanism, refer to FIG. 2. Under the stress condition of excess iron ions, the iron metabolism in wild-type (WT) host cells or FTH1 gene-knockout (FTH1−/−) host cells will be abnormal, and at the same time, it will also lead to the accumulation of a large number of cell membrane lipid peroxidation products (e.g., lipid reactive oxygen species (ROS)) in the cell, thereby inducing cell death. On the other hand, the transfected host cell with the expression vector has the FTH1 gene, which can replicate the vector in large quantities and translate into ferritin. Therefore, even under the stress condition of excess iron ions, the transfected host cell can survive. It is worth noting that since the expression vector further carries the gene encoding the target protein (indicated by GOI), the host cell will also translate the target protein. In other words, the addition of iron ions can also screen out the host cells expressing the target protein. Through the effect of iron ions inducing ferroptosis, the aforementioned screening mechanism can have the dual effect of improving the screening efficiency of the gene encoding the target protein and the mass production of the target protein.

In accordance with some embodiments, the concentration of iron ions added to the medium may be about 100 µM to about 1.5 mM, or about 125 µM to about 1 mM, for example, about 250 µM, about 500 µM, or about 750 µM, but it is not limited thereto. In accordance with some embodiments, the iron ions may include divalent iron ions or trivalent iron ions. In accordance with some embodiments, the source of iron ions may include ferric sulfate ($Fe_2(SO_4)_3$), ferrous sulfate ($FeSO_4$), ferric ammonium citrate ($C_6H_8FeNO_7$), ferric citrate ($C_6H_5FeO_7$), ferric chloride ($FeCl_3$), ferric nitrate ($Fe(NO_3)_3$), iron oxalate ($Fe_2(C_2O_4)_3$), ferric phosphate ($FePO_4$), or other suitable sources, but it is not limited thereto. In accordance with different embodiments, the appropriate concentration range of iron ions can be adjusted according to the type of host cells used.

In accordance with some embodiments, the surviving host cells can be screened by any method known in the art to obtain the host cells expressing the target protein.

Furthermore, in accordance with some embodiments, the step of screening the host cells may further include adding an ferroptosis inducer in the medium. The use of ferroptosis inducer in the screening process can further promote the occurrence of ferroptosis, improve the sensitivity of cells to iron ions, and optimize the screening effect.

In accordance with some embodiments, the ferroptosis inducer may be an inducer that can exert dual effects involving iron oxidation and loss of GPX4 enzymatic activity to induce ferroptosis. For example, in accordance with some embodiments, the ferroptosis inducer may include $FINO_2$ (ferroptosis inducer endoperoxide), Erastin, piperazine Erastin (PE), imidazole ketone Erastin (IKE), sulfasalazine, sorafenib, glutamate, RAS-selective lethal 3 (RSL3), molecular libraries 162 (ML162), diverse pharmacological inhibitor (DPI) compounds 7, 10, 12, 13, 17, 18, 19, ferroptosis inducer 56 (FIN56), caspase-independent lethal 56 (CIL56), or other suitable ferroptosis inducers, but it is not limited thereto. In accordance with some embodiments, the ferroptosis inducer may be added at a concentration of about 0.5 µM to about 2 mM, or about 1 µM to about 1.8 mM, or about 10 µM to about 1.5 mM, or about 20 µM to about 1.2 mM, or about 50 µM to about 1 mM, for example, about 100 µM, about 200 µM, about 300 µM, about 400 µM, about 500 µM, about 600 µM, about 700 µM, about 800 µM, or about 900 µM, but it is not limited thereto. In accordance with different embodiments, the appropriate concentration range of the ferroptosis inducer can be adjusted according to the type of host cells used.

Furthermore, in accordance with some embodiments, the step of screening the host cells may further include adding fatty acids in the medium. The addition of fatty acids to the medium can further promote the production of lipid peroxidation products (e.g., ROS), thereby inducing ferroptosis, and optimizing the screening effect.

The fatty acids may include saturated fatty acids, unsaturated fatty acids, or a combination thereof. In accordance with some embodiments, the fatty acid may include palmitic acid (PA), linoleic acid (LA), arachidonic acid (AA), eicosapentaenoic acid (EPA), docosapentaenoic acid (DPA), docosahexaenoic acid (DHA), or other suitable fatty acids, but it is not limited thereto. In accordance with some embodiments, the fatty acid may be added at a concentration of about 50 μM to about 500 μM, or about 60 μM to about 190 μM, or about 70 μM to about 180 μM, for example, about 80 μM, about 90 μM, about 100 μM, about 110 μM, about 120 μM, about 130 μM, about 140 μM, about 150 μM, about 160 μM, or about 170 μM, but it is not limited thereto. In accordance with different embodiments, the appropriate concentration range of fatty acid can be adjusted according to the type of host cells used.

Furthermore, in accordance with some embodiments, the host cell may be an FTH1 gene-knockout cell. In accordance with some embodiments, the use of FTH1 gene-knockout host cells can further enhance the difference in tolerance of host cells with or without a vector to ferroptosis, so that the screening effect is more obvious. In accordance with some embodiments, gene knockout cell lines can be constructed by CRISPR/Cas9 technique, but the present disclosure is not limited thereto.

As mentioned above, in accordance with the embodiments of the present disclosure, the method for screening host cells expressing the target protein uses FTH1 gene as a selection marker in combination with the medium of a specific formula to screen for the cells including the gene encoding target protein. The screening method thus established can rapidly screen and obtain specific cells stably expressing exogenous recombinant genes, and can promote the expression of exogenous genes in cells.

In addition, in accordance with the embodiments of the present disclosure, a method for establishing a stable cell line is also provided. The method includes the following steps: (a) providing an expression vector, the expression vector including a promoter, a gene encoding a target protein and an FTH1 gene; (b) transfecting host cells with the expression vector; (c) culturing the host cells in a medium; and (d) adding iron ions in the medium, and continuously culturing the host cells in the medium containing iron ions for a period of time, to screen and obtain a cell line that stably expresses the gene encoding the target protein.

Regarding the detailed descriptions of steps (a) to (c), reference can be made to the aforementioned method for screening host cells expressing the target protein, and will not be repeated herein. In accordance with some embodiments, after adding iron ions in the medium, the host cells are continuously cultured and iron ions are continuously supplemented to maintain the iron ion concentration in the medium, so as to continuously screen the cells to obtain a cell line that stably expresses the gene encoding the target protein.

In accordance with some embodiments, the host cells can be continuously screened and cultured for about 5 days to about 30 days, e.g., 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, or 29 days. Specifically, in accordance with some embodiments, after about 5 days to about 10 days of continuous culture and selection, 100% of the surviving host cells can carry the exogenous gene of the expression vector, i.e. the FTH1 gene and the gene encoding the target protein. Thereafter, the cells can be cultured in a medium containing iron ions to maintain their growth and maintain the expression of the gene encoding the target protein.

In accordance with some embodiments, after screening to obtain a cell line that stably expresses the gene encoding the target protein, the cell line can be continuously screened and expanded in an environment containing iron ions to establish a stable cell line. As mentioned above, the step of screening host cells may further include adding the ferroptosis inducer and fatty acids to the medium. In accordance with some embodiments, after establishing a stable cell line, the ferroptosis inducers and/or fatty acids may no longer be added to the medium.

As mentioned above, in accordance with some embodiments, the method for establishing a stable cell line uses FTH1 gene as a screening marker in combination with the medium of a specific formula, to obtain the cell line that stably expresses the gene encoded the target protein by screening through ferroptosis. This method can quickly obtain a cell line stably expressing the exogenous recombinant gene, and can promote the expression of the exogenous gene in the cell line. It is worth noting that the screened cell lines can stably express the target protein for a long time. For example, in accordance with some embodiments, nearly 100% of the screened cell lines express the target protein and can continuously express the target protein for about 160 days, about 200 days or even about a year or more.

In addition, in accordance with some embodiments of the present disclosure, a eukaryotic host cell is also provided, which is formed by transfection of the expression vector provided in the embodiments of the present disclosure. In accordance with some embodiments, the eukaryotic host cell may be a CHO cell, HEK293 cell, Hela cell, VERO cell, NS0 cell, or other suitable cells, but it is not limited thereto.

In accordance with some embodiments, a method for preparing a recombinant protein is also provided. The method includes the following steps: (a) culturing the eukaryotic host cell provided in the embodiments of the present disclosure in a medium; and (b) isolating the recombinant protein from the medium. In accordance with some embodiments, the recombinant protein may include an antibody, but it is not limited thereto. In accordance with some embodiments, the eukaryotic host cell described above can be cultured under conditions suitable for antibody expression, and the antibody can be recovered from the host cell (or medium of the host cell).

It is worth noting that the eukaryotic host cells formed by the transfection of the expression vector provided in the embodiments of the present disclosure can stably express the recombinant protein drug, and promote the mass production of the target recombinant protein drug.

In order to make the above-mentioned and other purposes, features and advantages of the present disclosure thorough and easy to understand, a number of preparation examples, examples, and comparative examples are given below, and are described in detail as follows, but they are not intended to limit the scope of the present disclosure.

Example 1: Relevance Verification Between the Expression of FTH1 Gene and Iron-Induced Ferroptosis In order to verify the relevance between FTH1 gene expression and iron-induced ferroptosis, the FTH1 gene was knocked out (knockout, KO) using a CRISPR/Cas9 technique and the FTH1 gene was overexpressed (Plasmid Overexpression) using a vector transfection technique for functional verification.

First, the FTH1 gene-knockout CHOK1 cell line (FTH1-KO) was constructed using a CRISPR/Cas9 gene editing technique, and the guide ribonucleic acid (guide RNA) was designed using the FTH1 gene chromosome of Chinese hamster (CgFth1). Then, the complex CRISPR/Cas9 ribonucleoprotein (RNP) formed by Cas9 protein and the guide RNA was sent into the CHOK1 cell line by electroporation (NEPA21 Electroporator) for gene editing. Afterwards, single-cell screening and culture and gene sequencing of mutant strains were performed to confirm the mutant type, and protein analysis of mutant strains was performed with FTH1 antibody (ab65080, Abcam) using Western blotting to verify the expression of the FTH1 protein of cell lines. The results of nucleic acid sequencing and the Western blotting are shown in FIG. 3A and FIG. 3B, respectively.

Figure 3A:
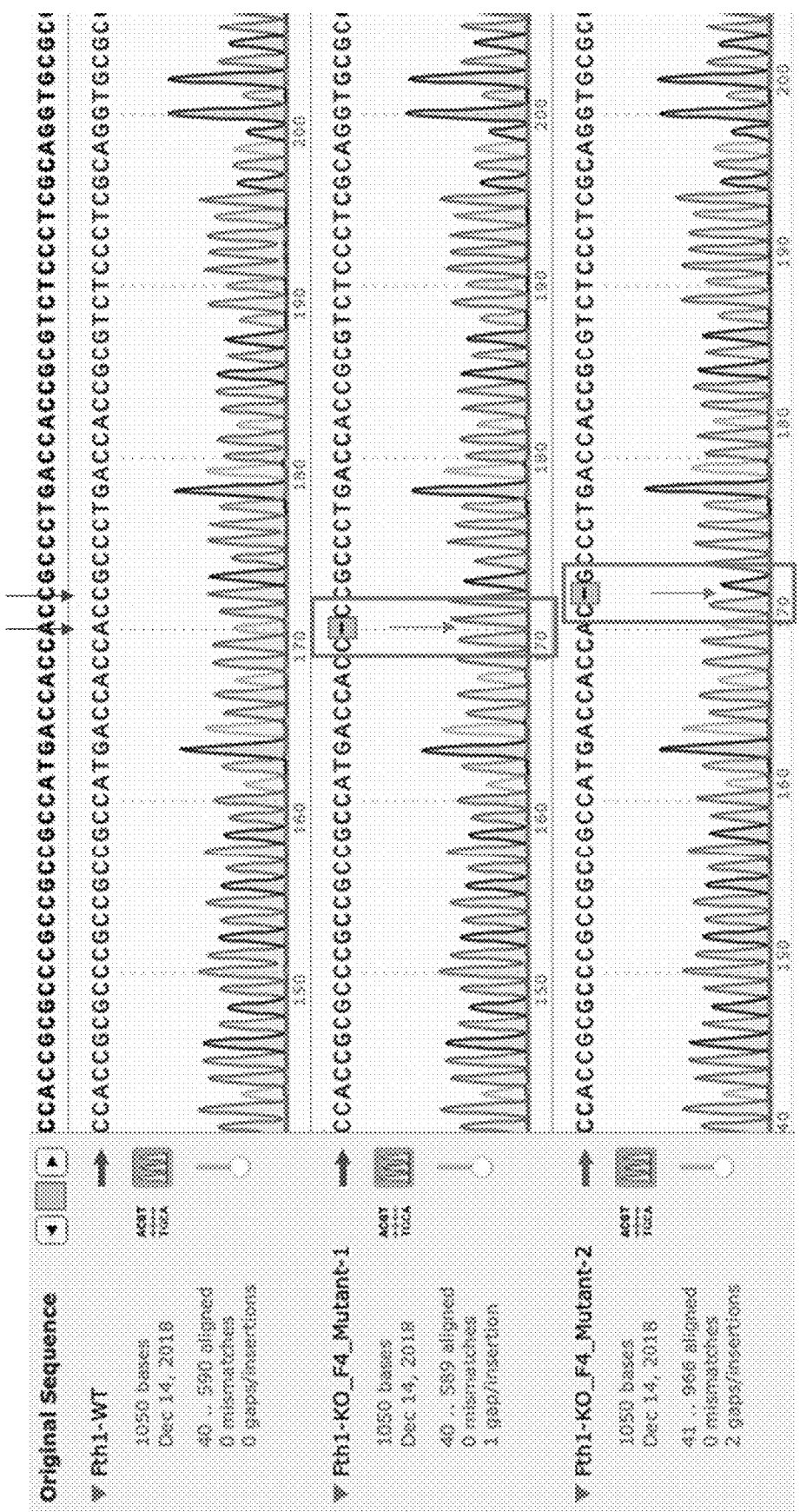
FIG. 3A shows a sequencing result of nucleic acid sequence of the CHOK1 cell line processed by CRISPR/Cas9 gene editing technique (CHOK1_Fth1_KO_F4) in accordance with some embodiments of the present disclosure.

Refer to FIG. 3A, the result of nucleic acid sequencing shows that the FTH1 gene-knockout cell line (F4) had a single nucleic acid deletion (single base deletion) on both paired gene chromosomes. Since two types of point mutations of single base deletion were located on the exon (Exon-1) of the FTH1 gene, it is predicted that a stop codon may be generated, causing the protein to fail to complete translation.

Figure 3B:
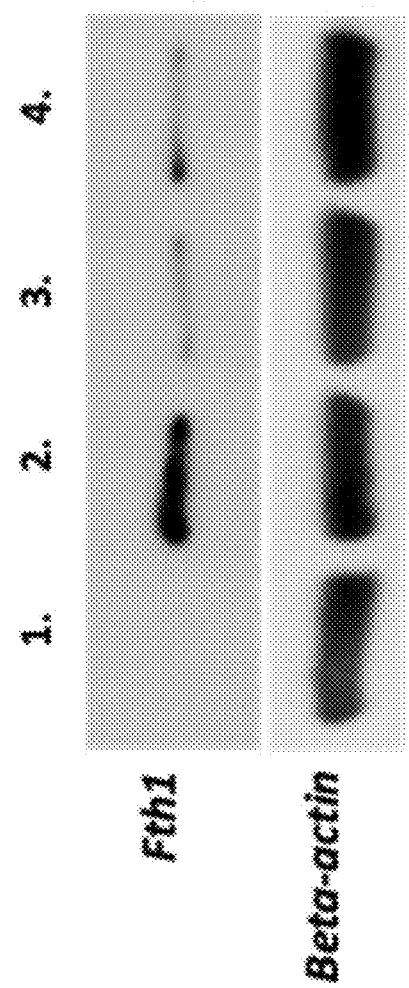
FIG. 3B shows a result of protein expression level of the CHOK1 cell lines analyzed by Western blotting method in accordance with some embodiments of the present disclosure (columns 1 to 4 respectively represent an FTH1 gene-knockout cell line (CHOK1_Fth1_KO_F4), a wild-type cell line (CHOK1_Fth1_WT), an FTH1 gene-edited cell line (CHOK1_Fth1_F20) and an FTH1 gene-edited cell line (CHOK1_Fth1_C16)).

Referring to FIG. 3B, columns 1 to 4 respectively represent the results of the FTH1 gene-knockout cell line (CHOK1_Fth1_KO_F4), the wild-type cell line (CHOK1_Fth1_WT), the FTH1 gene-edited cell line (CHOK1_Fth1_F20) and the FTH1 gene-edited cell line (CHOK1_Fth1_C16), and beta-actin serves as a control group. The results of Western blotting analysis showed that the expression of the protein was not detected in the CHOK1_Fth1_KO_F4 mutant cell line, indicating that the FTH1 gene was successfully knocked out in the CHOK1 cell line. That is, the FTH1 gene-knockout cell line was successfully established by CRISPR/Cas9 gene editing technique.

Then, two types of CHOK1 cell lines, Fth1_WT (CHOK1, BCRC) and Fth1_KO (Fth1_WT was the wild-type cell line; Fth1_KO was the FTH1 gene-knock out cell line), were respectively seeded in 96-well culture plates with $1\times10^4$ cells/well. After adherent culture in F12 medium (Ham's F-12 Nutrient Mix, Gibco) containing 10% FBS for 24 hours, different concentrations of ferrous sulfate ($FeSO_4$) were added as a source of iron ions to induce ferroptosis. On the 5th day (120 hours) after treatment, cell viability was detected with AlamarBlue™ cell viability reagent (Thermo Fisher Scientific Inc.). The percentage of cell viability under the treatment of different concentrations of iron ions was calculated by dividing the fluorescence detection readings (Ex/Em: 560 nm/590 nm) and the fluorescence value of the untreated negative control group. The experimental results are shown in FIG. 4A.

Furthermore, two types of CHOK1 cell lines, Fth1-WT (CHOK1, BCRC) and Fth1-KO, were seeded in 96-well culture plates with $1\times10^4$ cells/well respectively. After adherent culture in F12 medium (Ham's F-12 Nutrient Mix, Gibco) containing 10% FBS for 24 hours, the transfection of the vector (pcDNA3.1-CMV-CgFth1-p2A-EGFP) was carried out with Lipofectamine 3000 (Thermo Fisher Scientific Inc.) to promote the overexpression of the FTH1 gene. 24 hours after the DNA transfection of the vector, ferroptosis was induced by adding different concentrations of ferrous sulfate ($FeSO_4$). On the 5th day (120 hours) after treatment, cell viability was detected with AlamarBlue™ cell viability reagent (Thermo Fisher Scientific Inc.). By detecting the fluorescence readings (Ex/Em: 560 nm/590 nm), the effects of two CHOK1 cell lines on iron-induced ferroptosis under the condition of FTH1 overexpression were compared. The experimental results are shown in FIG. 4B.

Figure 4A:
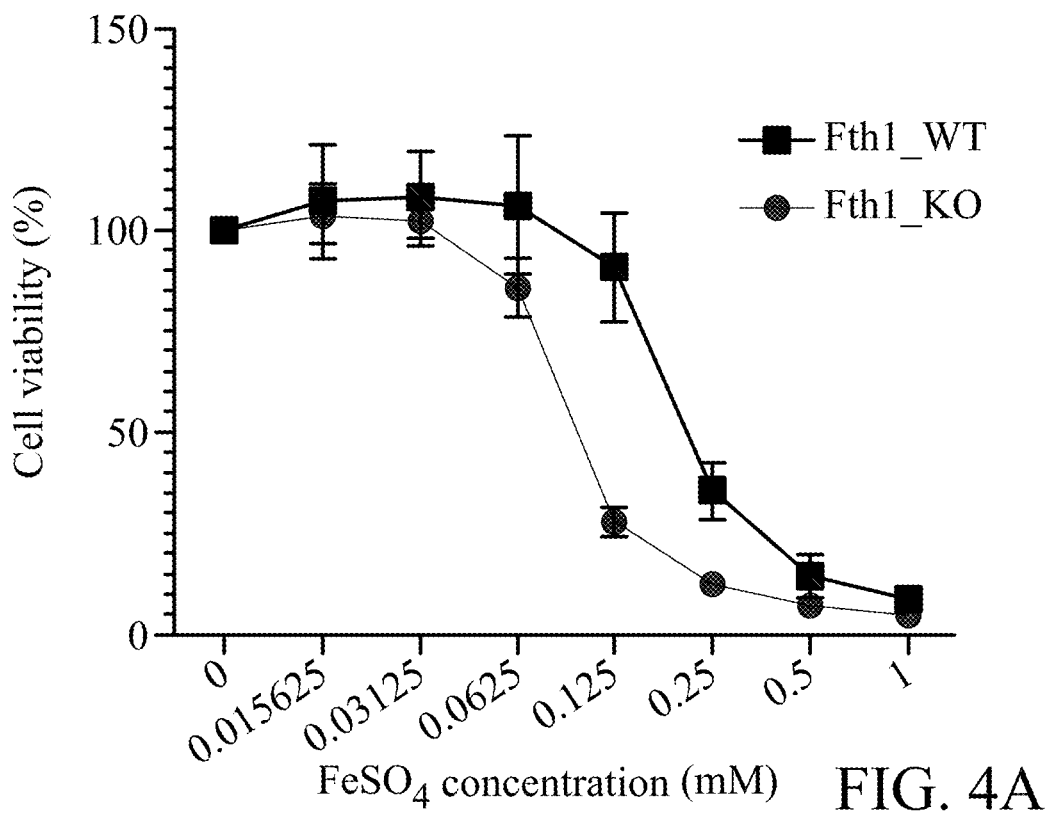
FIG. 4A shows an analysis result of cell viability of the CHOK1 cell lines Fth1_WT and Fth1_KO after treated with different concentrations of iron ions in accordance with some embodiments of the present disclosure.
Figure 4B:
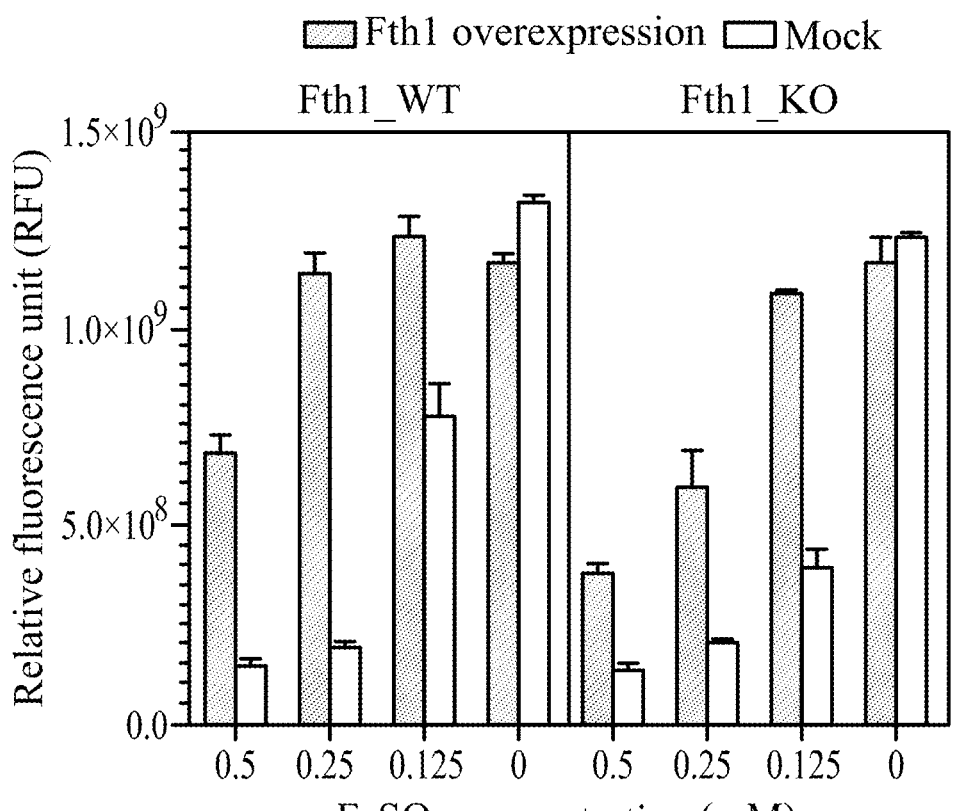
FIG. 4B shows an analysis result of the effects of the CHOK1 cell lines Fth1_WT and Fth1_KO under the condition of overexpression of FTH1 gene on iron ion-induced ferroptosis in accordance with some embodiments of the present disclosure.

As shown in FIG. 4A and FIG. 4B, the experimental results confirm that the knockout of the FTH1 gene makes the CHO cell lines more sensitive to iron-induced ferroptosis. In addition, the strategy of overexpressing exogenous FTH1 gene by the vector can significantly slow down iron-induced ferroptosis. According to the above results, it can be seen that the expression of FTH1 gene in cells is highly correlated with iron-induced ferroptosis.

Example 2: Tolerance Change of FTH1 Gene Expression in Cells Under the Effects of a Ferroptosis Inducer In order to verify the relevance of the expression level of FTH1 gene and ferroptosis, two different iron ion sources, ferric ammonium citrate ($C_6H_8FeNO_7$) and ferrous sulfate ($FeSO_4$), were added to the cell culture broth, and the cells were treated with different concentrations of ferroptosis inducer $FINO_2$.

Two types of CHOK1 cell lines, Fth1_WT and Fth1_KO, were seeded in 96-well culture plates with $1\times10^4$ cells/well respectively. After 24 hours of adherent culture, 200 μM of ferric ammonium citrate ($C_6H_8FeNO_7$) and ferrous sulfate ($FeSO_4$) were respectively added to F12 medium (Ham's F-12 Nutrient Mix, Gibco) containing 10% FBS, and at the same time different doses of ferroptosis inducer $FINO_2$ (CAS #869298-31-7; Cayman Chemical) were added to induce ferroptosis. After 24 hours of action, cell viability was detected with AlamarBlue™ cell viability reagent (Thermo Fisher Scientific Inc.). By detecting the fluorescence readings (Ex/Em: 560 nm/590 nm), the differences of ferroptosis occurring in the two CHOK1 cell lines were compared. The experimental results are shown in FIG. 5.

Figure 5:
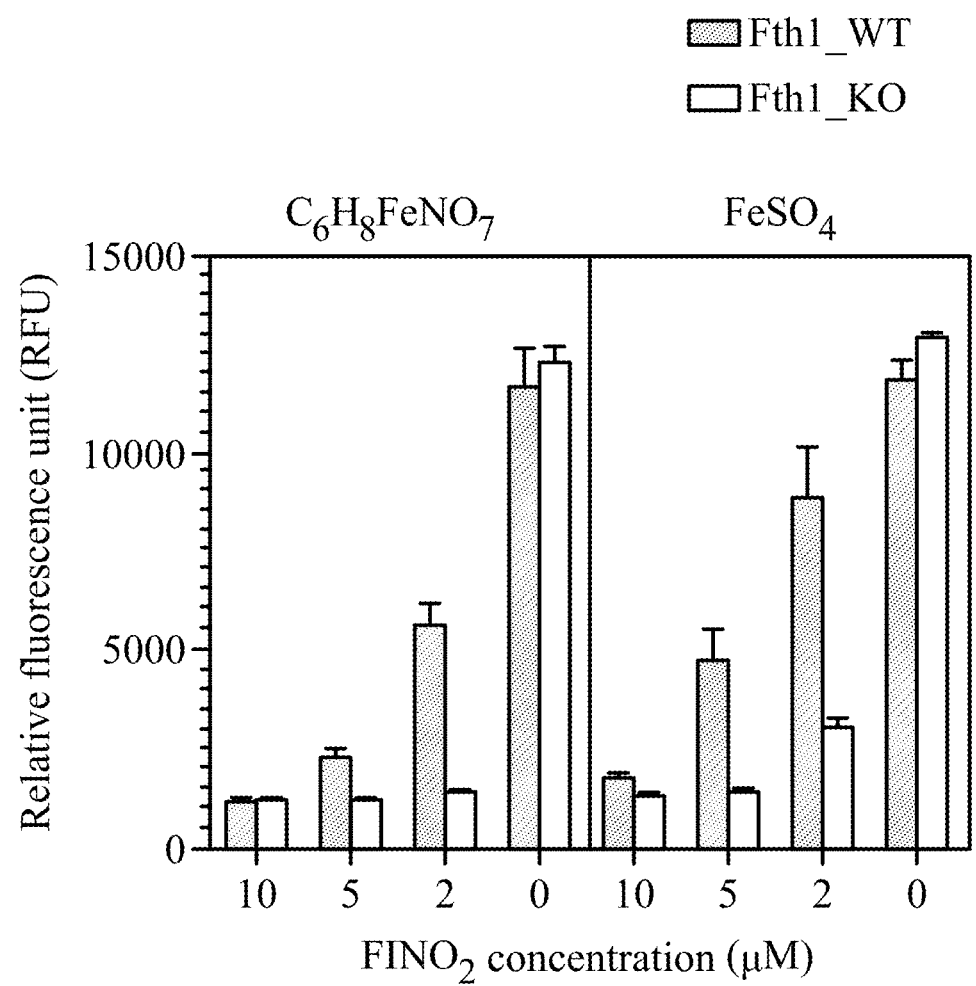
FIG. 5 shows an analysis result of the effects of the CHOK1 cell lines Fth1_WT and Fth1_KO treated with different iron ion sources ($C_6H_8FeNO_7$ and $FeSO_4$) and different concentrations of ferroptosis inducer $FINO_2$ on iron ion-induced ferroptosis in accordance with some embodiments of the present disclosure.

As shown in FIG. 5, the experimental results show that both the above-mentioned two sources of iron ions can induce ferroptosis under the action of the ferroptosis inducer. The expression of FTH1 gene is negatively correlated with the degree of ferroptosis, and the addition of ferroptosis inducers can improve the cytotoxic effect, indicating that FTH1 gene can protect CHOK1 cells under the action of ferroptosis inducers and inhibit the occurrence of ferroptosis.

Example 3: Test of Screening Condition for Induction of Iron-Induced Ferroptosis In order to construct a high-efficiency cell line screening method, the ferroptosis inducer $FINO_2$ was combined with the addition of iron ions $FeSO_4$ and the presence or absence of fatty acid palmitic acid (PA) to carry out the cytotoxicity test, to find out a suitable medium formulation for cell line screening.

Two types of CHOK1 cell lines, Fth1_WT (CHOK1, BCRC) and Fth1_KO, were respectively seeded in 96-well culture plates with $1\times10^4$ cells/well. After 24 hours of adherent culture, 125 μM ferrous sulfate ($FeSO_4$) was added to F12 medium (Ham's F-12 Nutrient Mix, Gibco), and at the same time different doses of ferroptosis inducer $FINO_2$ and/or fatty acid PA (Palmitic acid, P0500Sigma-Aldrich) were added to induce ferroptosis. After 24 hours of action, cell viability was detected with AlamarBlue™ cell viability reagent (Thermo Fisher Scientific Inc.). By detecting the fluorescence readings (Ex/Em: 560 nm/590 nm), the effects of inducing ferroptosis of the two CHOK1 cell lines on under different screening medium formulations were compared. The experimental results are shown in FIGS. 6A to 6D.

Refer to FIG. 6A, in the condition that the medium simultaneously contained $FINO_2$, 125 μM $FeSO_4$, and fatty acid PA, the Fth1_KO cell line caused significant cytotoxic effect in 48 hours under the action of 2 μM FIN04. Referring to FIG. 6B, in the condition that only $FINO_2$ and 125 μM $FeSO_4$ were added, the Fth1_KO cell line caused significant cytotoxic effect under the addition of 5 μM $FINO_2$, and there was no obvious difference between the Fth1_WT cell line and the Fth1_KO cell line. Referring to FIG. 6C, $FINO_2$ and fatty acid PA did not cause cytotoxicity without the addition of iron ions $FeSO_4$. Furthermore, referring to FIG. 6D, in the condition that only $FINO_2$ was added, even a dose of 5 μM did not cause significant cytotoxicity.

According to the aforementioned experimental results, the occurrence of ferroptosis, in the condition of adding iron ions, $FINO_2$ and fatty acids, can cause obvious cytotoxicity effect, and the addition of $FINO_2$ and fatty acids has the effect of promoting iron ions-induced cytotoxicity.

Example 4: Establish FTH1 Recombinant Protein Expression Vector for Screening of Stable Cell Line The similarity of FTH1 gene among species is high. Among them, the amino acid sequences of the FTH1 genes of human (*Homo sapiens*), mouse (*Mus musculus*) and Chinese hamster (*Cricetulus griseus*) were compared. The results showed that the sequences of the three had more than 90% of similarity, and it can be inferred that their biological functions were similar. Therefore, the FTH1 genes of these three species were selected for the construction of subsequent expression vectors.

Figure 7A:
FIGS. 7A to 7C show schematic diagrams of the constructed expression vectors pCDNA3.1-CMV-cgFth1-p2A-EGFP, pCDNA3.1-CMV-mFth1-p2A-EGFP and pCDNA3.1-CMV-hFth1-p2A-EGFP in accordance with some embodiments of the present disclosure.
Figure 7B:
Figure 7C:
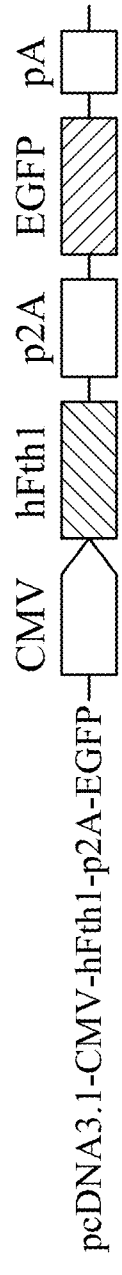

Referring to FIGS. 7A to 7C, FIGS. 7A to 7C show schematic diagrams of the expression vectors constructed by inserting Chinese hamster FTH1 gene (cgFth1), mouse FTH1 gene (mFth1) and human FTH1 gene (hFth1) based on pcDNA3.1-CMV vector, pcDNA3.1+P2A-eGFP (GenScript).

As shown in FIG. 7A, the pCDNA3.1-CMV-cgFth1-p2A-EGFP expression vector was based on the pCDNA3.1-CMV vector as a backbone, and the CMV promoter, cgFth1 gene, p2A peptide, EGFP reporter gene and pA terminator were inserted therein. The cgFth1 gene and the EGFP reporter gene was concatenated with the p2A peptide, the CMV promoter had the nucleic acid sequence shown in SEQ ID NO: 7, the cgFth1 gene had the nucleic acid sequence shown in SEQ ID NO: 4, and the p2A peptide had the nucleic acid sequence shown in SEQ ID NO: 8, the EGFP reporter gene had the nucleic acid sequence shown in SEQ ID NO: 9, and the pA terminator had the nucleic acid sequence shown in SEQ ID NO: 10.

As shown in FIG. 7B, the pCDNA3.1-CMV-mFth1-p2A-EGFP expression vector was based on the pCDNA3.1-CMV vector as a backbone, and the CMV promoter, mFth1 gene, p2A peptide, EGFP reporter gene and pA terminator were inserted therein. The mFth1 gene and the EGFP reporter gene were concatenated with the p2A peptide, the CMV promoter had the nucleic acid sequence shown in SEQ ID NO: 7, the mFth1 gene had the nucleic acid sequence shown in SEQ ID NO: 5, and the p2A peptide had the nucleic acid sequence shown in SEQ ID NO: 8, the EGFP reporter gene had the nucleic acid sequence shown in SEQ ID NO: 9, and the pA terminator had the nucleic acid sequence shown in SEQ ID NO: 10.

As shown in FIG. 7C, the pCDNA3.1-CMV-hFth1-p2A-EGFP expression vector was based on the pCDNA3.1-CMV vector as a backbone, and the CMV promoter, hFth1 gene, p2A peptide, EGFP reporter gene and pA terminator were inserted therein. The hFth1 gene and the EGFP reporter gene were concatenated with the p2A peptide, the CMV promoter had the nucleic acid sequence shown in SEQ ID NO: 7, the hFth1 gene had the nucleic acid sequence shown in SEQ ID NO: 6, and the p2A peptide had the nucleic acid sequence shown in SEQ ID NO: 8, the EGFP reporter gene had the nucleic acid sequence shown in SEQ ID NO: 9, and the pA terminator had the nucleic acid sequence shown in SEQ ID NO: 10.

Figure 8:
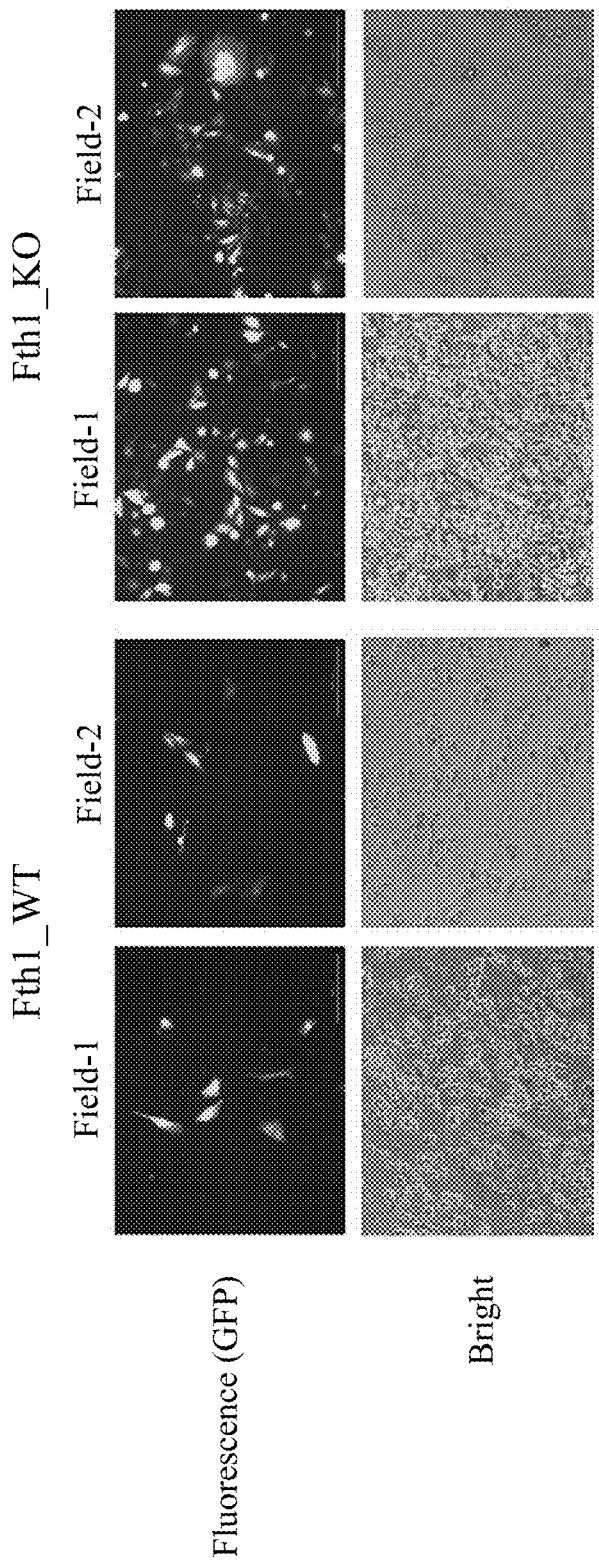
FIG. 8 shows analysis results of fluorescent protein expression of the CHOK1 cell lines Fth1_WT and Fth1_KO transfected with pCDNA3.1-CMV-cgFth1-p2A-EGFP expression vector in accordance with some embodiments of the present disclosure.

In order to verify that the overexpression of FTH1 gene can be used for the screening of stable cell lines, the pCDNA3.1-CMV-cgFth1-p2A-EGFP expression vector was used to transfect to the CHOK1 cell lines Fth1_WT (CHOK1, BCRC) and Fth1_KO respectively. $1\times10^6$ of cells were taken and electroporated (2 mm cuvette, NEPA21 Electroporator) at 125V for 24 hours to promote the overexpression of the Fth1 gene. In addition, 24 hours after the transfection of the vector, ferroptosis was induced by adding high doses of ferrous sulfate ($FeSO_4$, 500 μM). Refer to the fluorescent microscope observation results shown in FIG. 8. After 14 days of treatment, the cell lines with EGFP fluorescent expression were gradually screened out. Therefore, it was confirmed that the FTH1 recombinant protein expression vector and the addition of iron ions indeed had the effect of screening stable cell lines, and the Fth1_KO were more dependent on the retention of FTH1 exogenous genes than the Fth1_WT cells.

Example 5: Efficiency Comparison of FTH1 Gene of Different Species for Screening System In order to further verify that the FTH1 gene of different species origin can be used for the screening of stable cell line, the CHOK1 cell line and the HEK293T cell line were used as host cells, and the pCDNA3.1-CMV-cgFth1-p2A-EGFP expression vector, pCDNA3.1-CMV-mFth1-p2A-EGFP expression vector and pCDNA3.1-CMV-hFth1-p2A-EGFP expression vector were used to carry out experimental verification.

The CHOK1 cell line was seeded in the 96-well culture plate with $1\times10^4$ cells/well. After 24 hours of adherent culture in F12 medium (Ham's F-12 Nutrient Mix, Gibco) containing 10% FBS, the transfection of the aforementioned FTH1 gene expression vectors of the three species was carried out with Lipofectamine 3000 (Thermo Fisher Scientific Inc.), to promote the overexpression of the FTH1 gene. 24 hours after the DNA transfection of the vectors, 125 μM ferrous sulfate ($FeSO_4$) was added to the cell medium, and at the same time different doses of ferroptosis inducers ($FINO_2$, 0 μM to 5 μM) were added according to cell characteristics to induce ferroptosis. Fluorescent cells were counted with a Celigo Image Cytometer (Nexcelom). After 3 days (72 hours) of action, the fluorescent cells were counted with Celigo Image Cytometer (Nexcelom) and compared with the control group without $FINO_2$ treatment, thereby estimating the screening efficacy. The experimental results are shown in FIG. 9A.

The HEK293T cell line was seeded in the 96-well culture plate with $1\times10^4$ cells/well. After 24 hours of adherent culture in DMEM medium (Gibco) containing 10% FBS, the transfection of the aforementioned FTH1 gene expression vectors of the three species was carried out with Lipofectamine 3000 (Thermo Fisher Scientific Inc.), to promote the overexpression of the FTH1 gene. 24 hours after the DNA transfection of the vectors, 125 μM ferrous sulfate ($FeSO_4$) was added to the cell medium, and at the same time different doses of ferroptosis inducers ($FINO_2$, 0 μM to 5 μM) were added according to cell characteristics to induce ferroptosis. Fluorescent cells were counted with a Celigo Image Cytometer (Nexcelom). After 3 days (72 hours) of action, the fluorescent cells were counted with Celigo Image Cytometer (Nexcelom) and compared with the control group without $FINO_2$ treatment, thereby estimating the screening efficacy. The experimental results are shown in FIG. 9B.

Figure 9A:
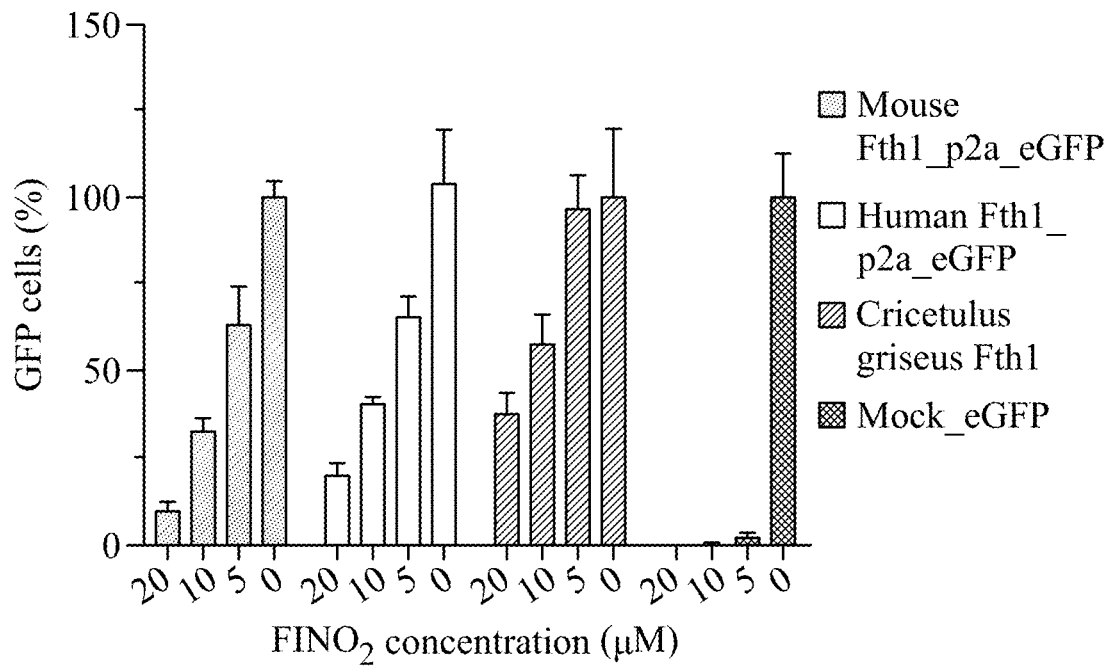
FIG. 9A shows analysis results of fluorescent cell counts of the CHOK1 cell lines transfected with the expression vectors pCDNA3.1-CMV-cgFth1-p2A-EGFP, pCDNA3.1-CMV-mFth1-p2A-EGFP and pCDNA3.1-CMV-hFth1-p2A-EGFP under the condition of iron ion-induced ferroptosis in accordance with some embodiments of the present disclosure.
Figure 9B:
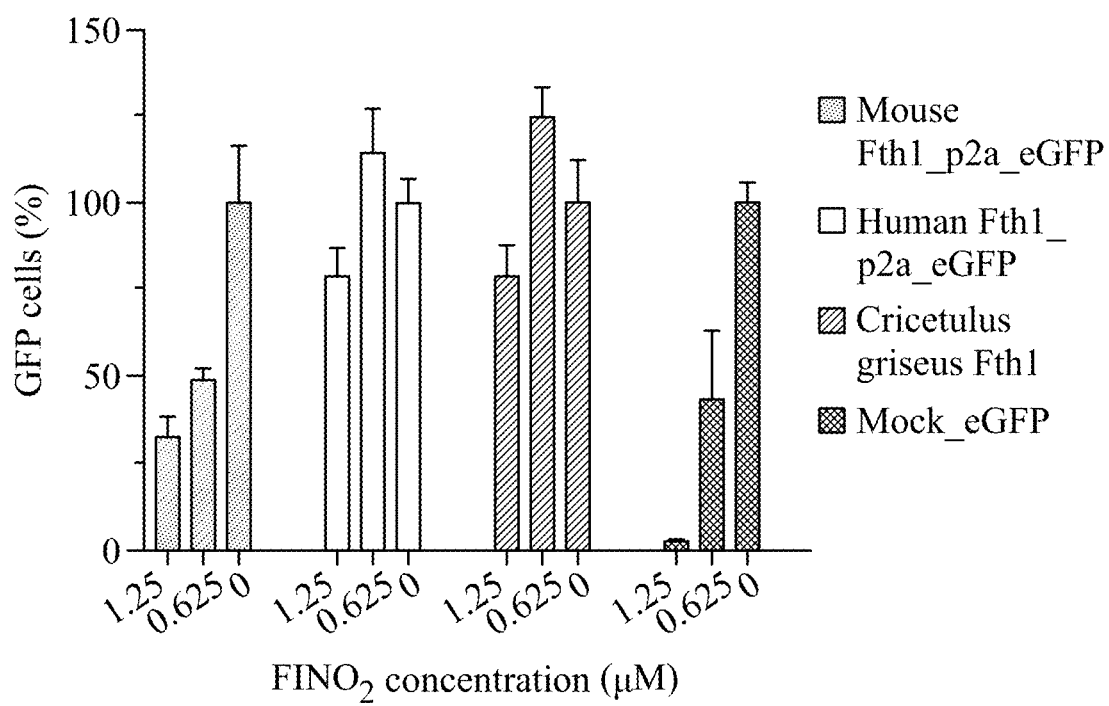
FIG. 9B shows analysis results of fluorescent cell counts of the HEK293T cell lines transfected with the expression vectors pCDNA3.1-CMV-cgFth1-p2A-EGFP, pCDNA3.1-CMV-mFth1-p2A-EGFP and pCDNA3.1-CMV-hFth1-p2A-EGFP under the condition of iron ion-induced ferroptosis in accordance with some embodiments of the present disclosure.

According to the results of FIG. 9A and FIG. 9B, it can be seen that in the presence of iron ions and ferroptosis inducers, for the expression vectors constructed with the FTH1 genes of Chinese hamster, mouse and human, compared to the Mock vector (blank control group), the expression vectors containing the FTH1 gene can promote the resistance of the transfected cell lines to apoptosis and maintain the expression of the exogenous gene (EGFP reporter gene). The results confirmed that the FTH1 gene derived from the three species all can be used in the screening of exogenous gene expression cell lines.

Example 6: Efficacy Evaluation of Screening System for Establishing Stable Cell Lines-1

According to the verification experiment results of the previous embodiment, a general flow process of the screening system for establishing the cell line is as follows: the expression vector is sent to the host cells for expression, after culturing the host cells for 24 hours, the screening formula (iron ions, ferroptosis inducers, fatty acids) was added for culture and screening, and after about 8 days of screening, about 100% of the cells can express the exogenous genes (for example, EGFP reporter genes), and then the cells are maintained in the medium formulation containing iron ions (500 µM ferrous sulfate or 1 mM ferric ammonium citrate) to maintain cell growth and expression of exogenous genes.

According to the aforementioned screening system, the CHOK1 cell lines Fth1-WT (CHOK1, BCRC) and Fth1-KO (CRISPR/Cas9 mediated knockout) were seeded in 96-well culture plates with $1\times10^4$ cells/well respectively. After 24 hours of adherent culture in F12 medium (Ham's F-12 Nutrient Mix, Gibco) containing 10% FBS, the transfection of vector (pCDNA3.1-CMV-cgFth1-p2A-EGFP) was carried out with Lipofectamine 3000 (Thermo Fisher Scientific Inc.) to promote the overexpression of FTH1 gene. 24 hours after the DNA transfection of the vectors, 125 µM ferrous sulfate ($FeSO_4$) was added to the cell culture broth, and at the same time different doses of ferroptosis inducers $FINO_2$ (0 µM to 20 µM) were added to induce ferroptosis. After 3 days (72 hours) of action, the Celigo Image Cytometer (Nexcelom) was used to analyze the cell morphology, viability, cell count, fluorescent cell count, and fluorescence quantification, thereby estimating the screening efficiency.

Figure 10:
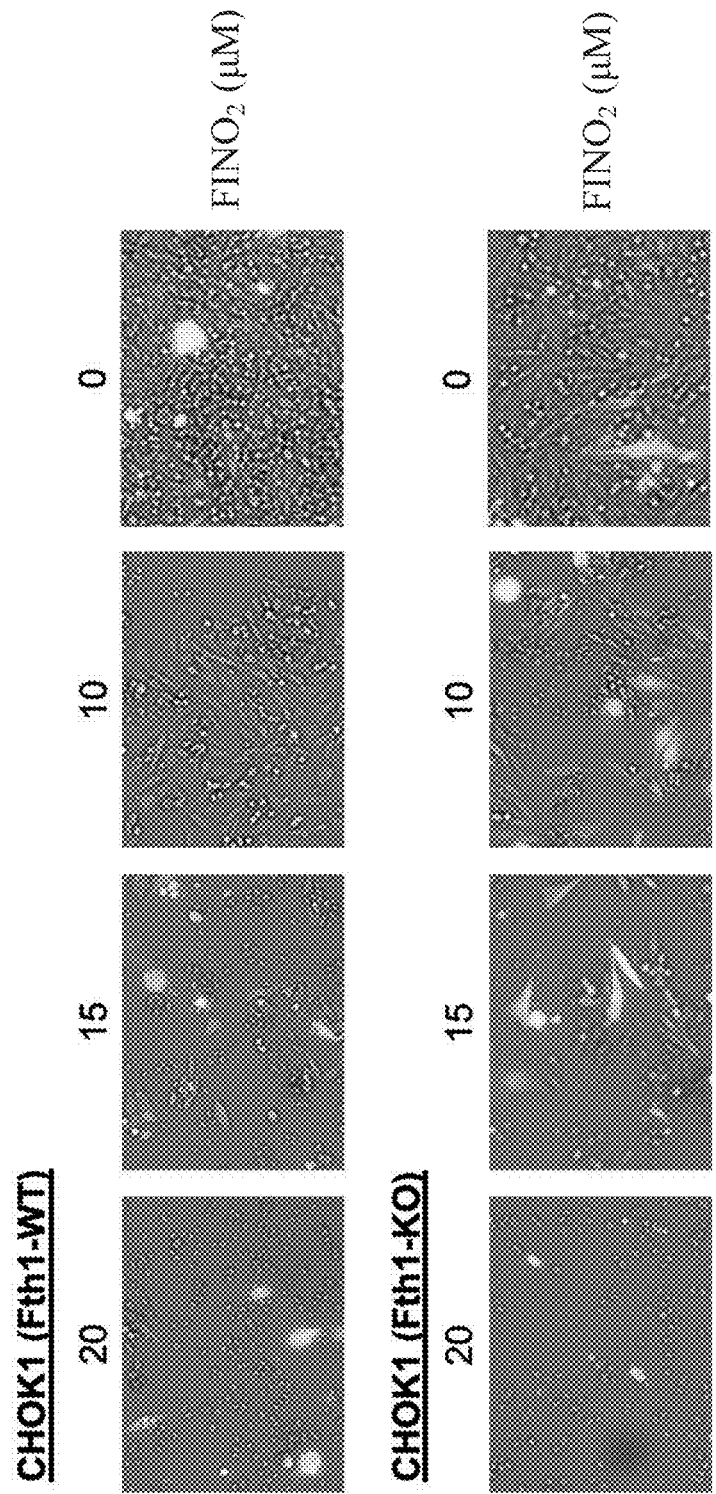
FIG. 10 shows analysis results of fluorescent protein expression of the CHOK1 cell lines the CHOK1 cell lines Fth1_WT and Fth1_KO transfected with the expression vector pCDNA3.1-CMV-cgFth1-p2A-EGFP under the condition of iron ion-induced ferroptosis in accordance with some embodiments of the present disclosure.

As shown in FIG. 10, the cytotoxic effect showed a dose-dependent change, and with the increase of the dose of the ferroptosis inducer, most cells experienced significant ferroptosis. Among them, cells expressing fluorescent proteins had higher tolerance to screening and had a better survival advantage. It can be seen that the expression of the expression vector constructed in the Examples of the present disclosure in the host cells can enhance the cell's tolerance to ferroptosis induced by the screening formula. In addition, in the condition of high dose of ferroptosis inducer (>15 µM), the cell screening rate can reach 100%.

Figure 11A:
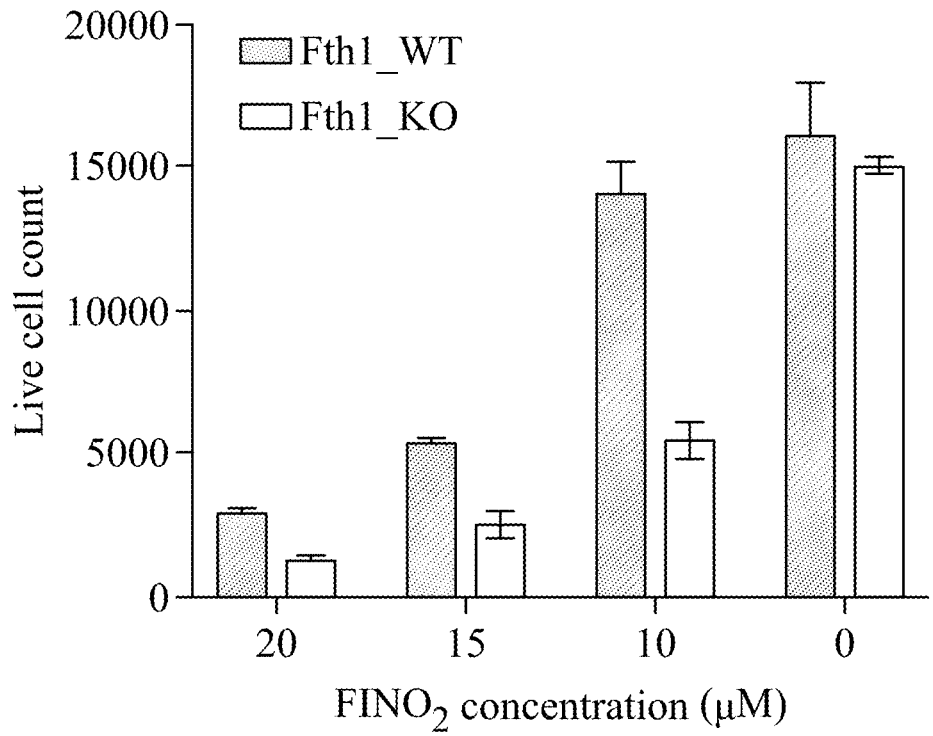
FIG. 11A and FIG. 11B show quantitative data analysis results obtained after the experimental results of FIG. 10 are processed in accordance with some embodiments of the present disclosure.
Figure 11B:
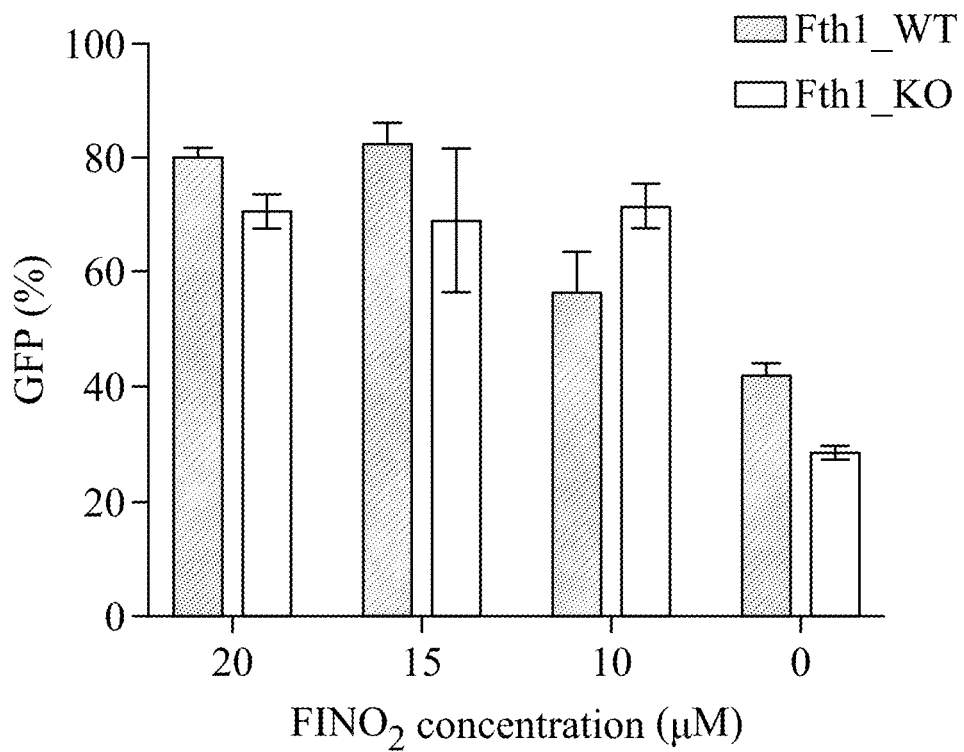

FIG. 11A and FIG. 11B present the quantitative data of the experimental results of FIG. 10. As shown in FIG. 11A, the increased dose of $FINO_2$ in the screening formula was negatively correlated with overall cell viability. As shown in FIG. 11B, the increased dose of $FINO_2$ in the screening formula was positively correlated with the expression of exogenous genes (EGFP fluorescent protein), indicating that the vector system could endow the cell line with maintaining the expression of the exogenous gene.

Figure 12A:
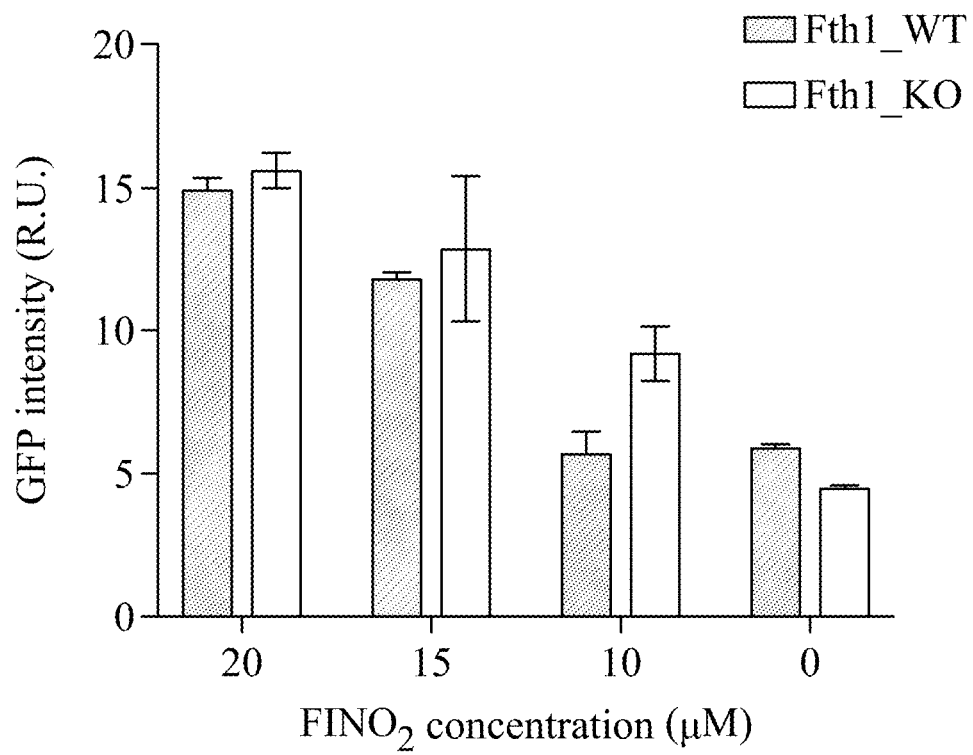
FIG. 12A and FIG. 12B show quantitative data analysis results obtained after the experimental results of FIG. 10 are processed in accordance with some embodiments of the present disclosure.
Figure 12B:
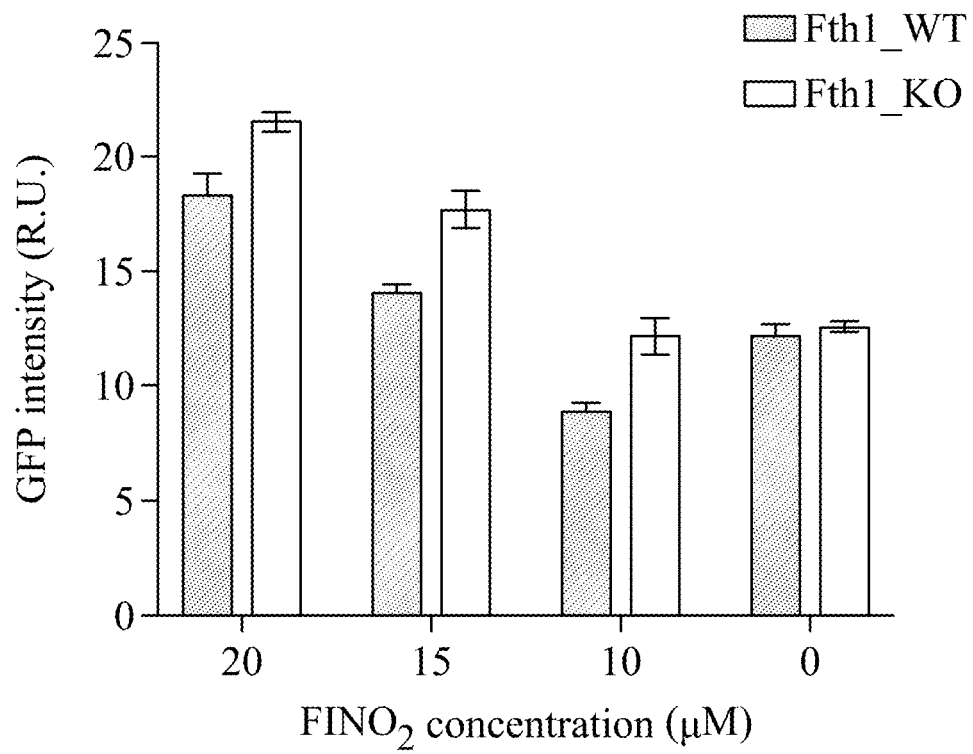

Refer to FIG. 12A and FIG. 12B. FIG. 12A and FIG. 12B present the quantitative data of the experimental results of FIG. 10, which compares the fluorescent expression level of surviving cells after screening (FIG. 12A) and the fluorescent expression level of fluorescent cells (FIG. 12B). The results showed that the cells that survived the screening had a strong fluorescent protein expression level, and the CHOK1 cell line Fth1_KO cell line also showed a higher fluorescent protein expression level. The above results confirm that the screening system established in the Examples of the present disclosure can help to maintain the expression of exogenous genes in cells, and has a good effect of recombinant protein expression.

Figure 13:
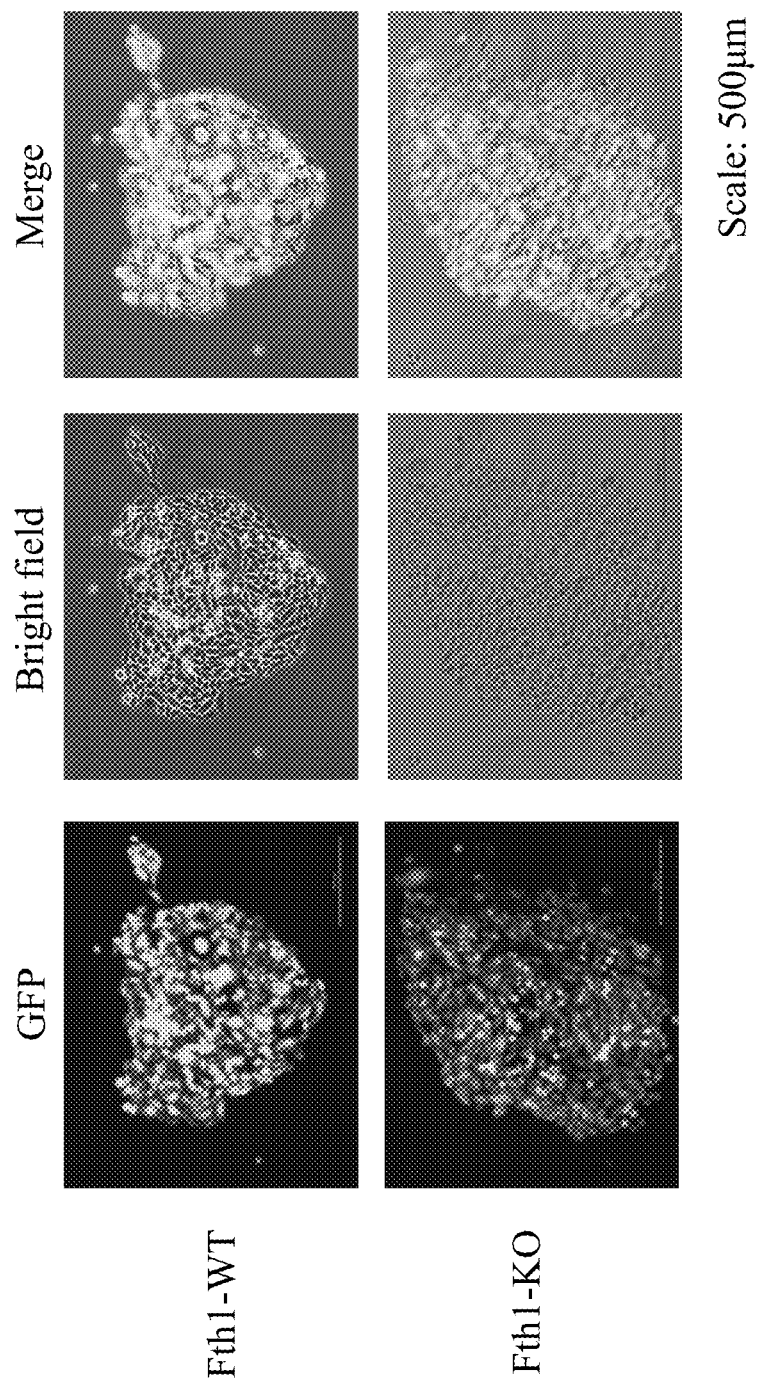
FIG. 13 shows analysis results of fluorescent protein expression of a single cell grown as a cell colony in a medium containing iron ions after screening in accordance with some embodiments of the present disclosure.

Furthermore, in order to verify the ability of the exogenous genes to maintain expression after screening, the screened cell lines in Example 6 were transferred to a 6-well culture plate for culture, and the screening drug $FINO_2$ was continuously added for 3 days of screening. Thereafter, the cells were maintained for continuous subculture in F12 medium (Ham's) containing 500 µM ferric sulfate. Refer to FIG. 13, which shows the results of the fluorescence expression of a single cell growing into a cell colony in the medium containing iron ions (500 µM ferrous sulfate) after the above-mentioned screening. As shown in FIG. 13, the proportion of cells expressing the fluorescent proteins could reach 100%.

Example 7: Efficacy Evaluation of Screening System for Establishing Stable Cell Lines-2

In order to verify the ability of the exogenous gene to maintain expression, after the screening culture, the cells were maintained in F12 medium (Ham's) containing 500 µM ferric sulfate for continuous subculture, and the proportion of cells with fluorescent protein expression was assessed by flow cytometer, thereby verifying the efficacy of stable expression of exogenous genes.

Figure 14:
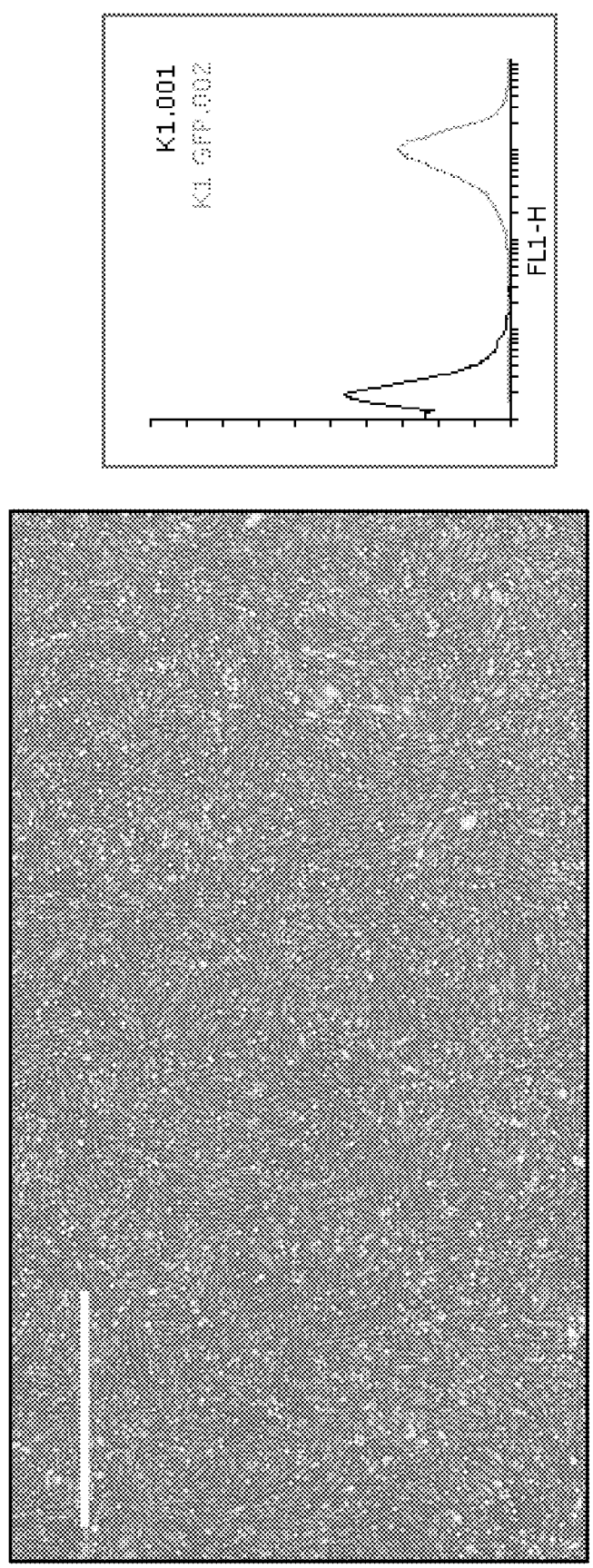
FIG. 14 shows an analysis result of the fluorescent protein expression of the screened CHOK1 cell line, whose FTH1 is WT after 160 days of continuous subculture.
Figure 15:
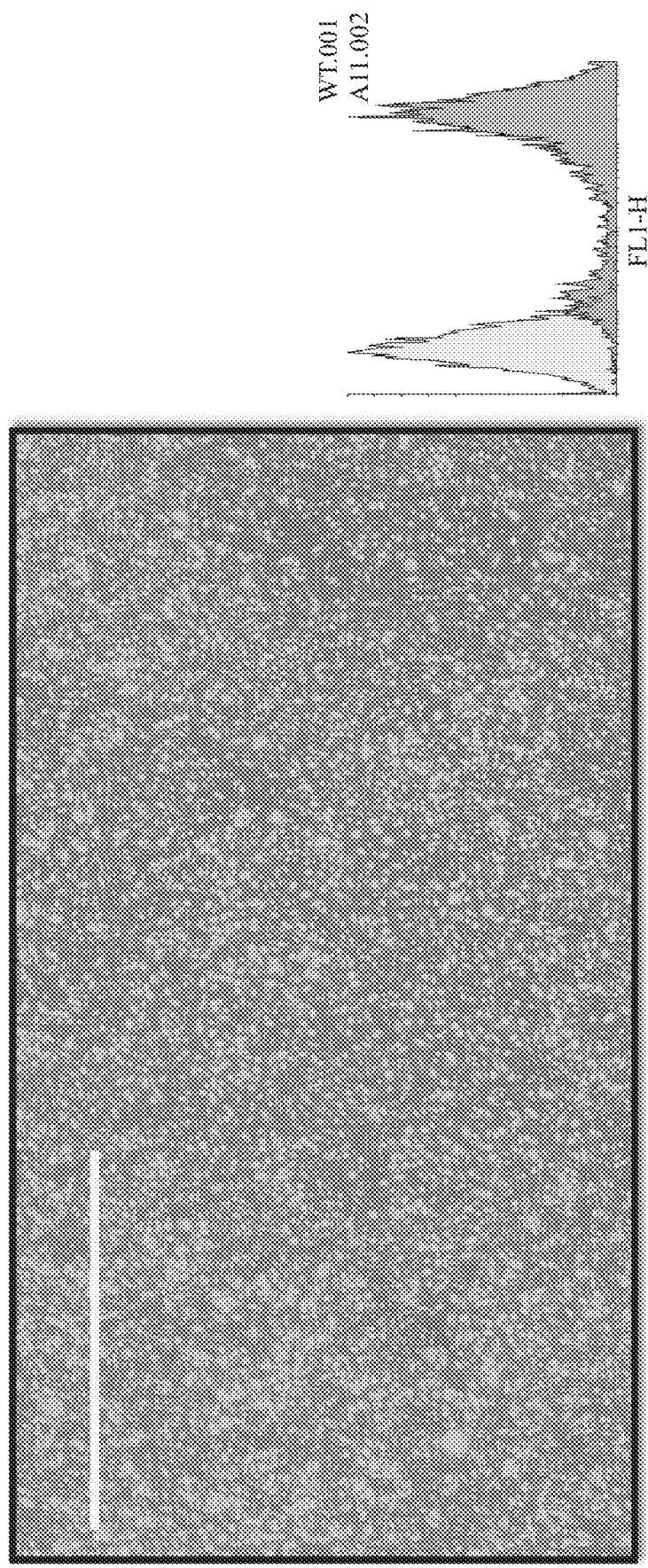
FIG. 15 shows an analysis result of the fluorescent protein expression of the screened CHOK1 cell line after 210 days of continuous subculture.

FIG. 14 and FIG. 15 show the results of fluorescence performance of the screened CHOK1_WT cell line after continuous subculture for 160 days and 210 days, respectively. As shown in FIG. 14 and FIG. 15, the results show that after 160 days and 210 days of continuous subculture, the proportion of cells expressing fluorescent proteins could still be maintained at 100%. It is shown that cell lines stably expressing exogenous genes can be established through the screening system in the Examples of the present disclosure.

Example 8: Efficacy Evaluation of Screening System for Establishing Stable Cell Lines-3

In order to verify that the screening system established in the Examples of the present disclosure can be applied to a variety of industrial-grade cell lines, further verification experiments were performed using the HEK293T cell line and VERO cell line.

The HEK293T cell line (HEK293T, ATCC) and the VERO cell line (Vero, CCL-81; ATCC) were seeded in 96-well culture plates with $1\times10^4$ cells/well respectively. After 24 hours of adherent culture in F12 medium (Ham's F-12 Nutrient Mix, Gibco) containing 10% FBS, the transfection of vectors (pCDNA3.1-CMV-cgFth1-p2A-EGFP and pCDNA3.1-CMV-p2A-EGFP_Mock, which served as a blank control group) were carried out with Lipofectamine 3000 (Thermo Fisher Scientific Inc.) to promote the overexpression of FTH1 gene. 24 hours after the DNA transfection of the vectors, 125 μM ferrous sulfate (FeSO$_4$) was added to the cell culture broth, and at the same time different doses of ferroptosis inducers FINO$_2$ (0 μM to 20 μM) were added to induce ferroptosis. After 3 days (72 hours) of action, the Celigo Image Cytometer (Nexcelom) was used to analyze the fluorescence cell count and fluorescence quantification, thereby estimating the screening efficiency. The results are shown in FIG. 16A and FIG. 16B.

Figure 16A:
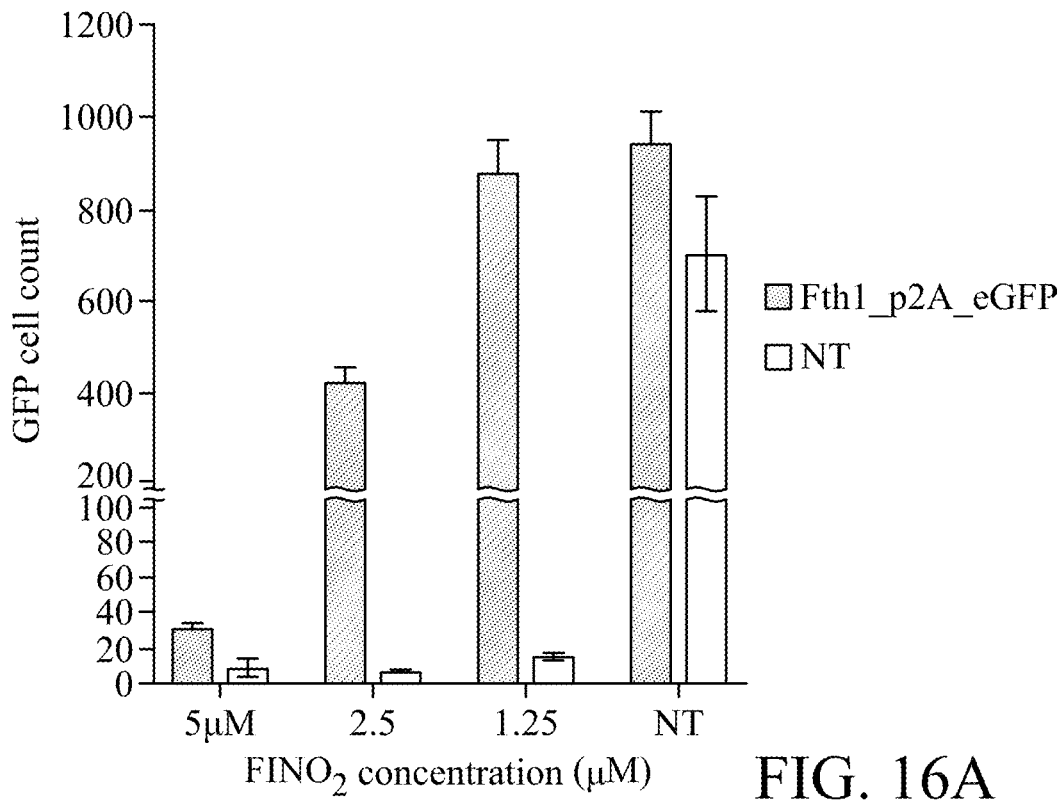
FIG. 16A shows analysis results of fluorescent cell counts of the HEK293T cell lines transfected with the expression vector pCDNA3.1-CMV-cgFth1-p2A-EGFP under the condition of iron ion-induced ferroptosis in accordance with some embodiments of the present disclosure.
Figure 16B:
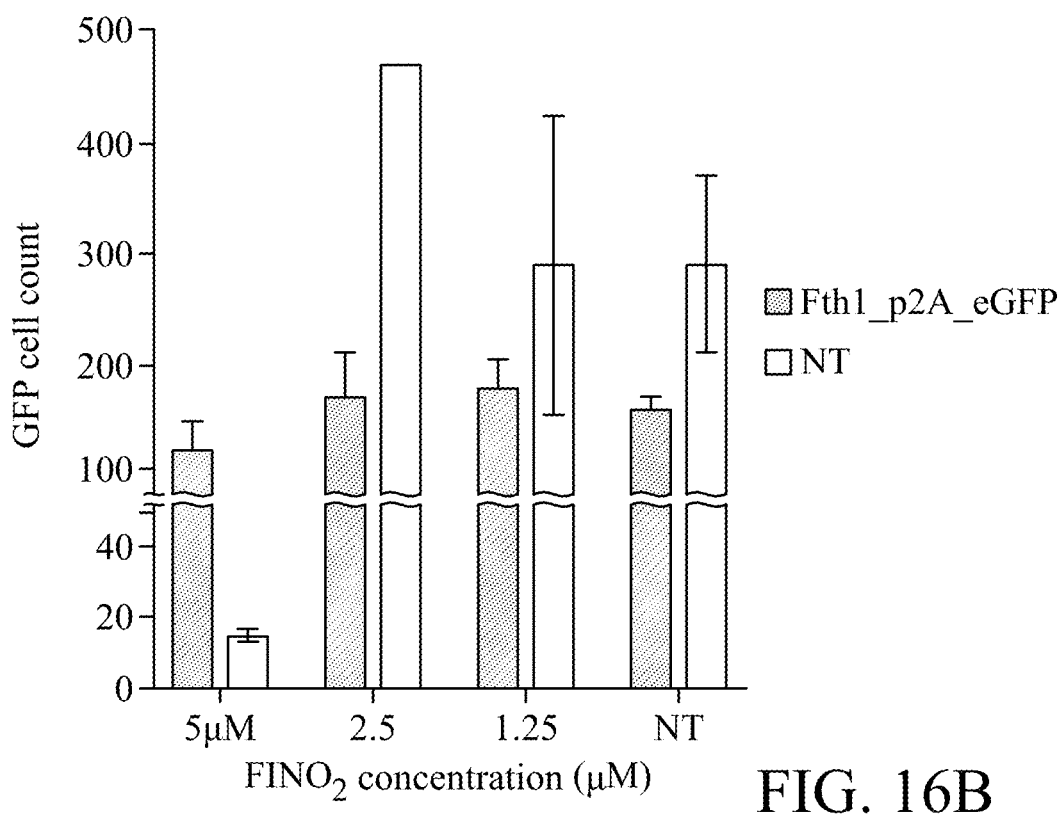
FIG. 16B shows analysis results of fluorescent cell counts of the VERO cell lines transfected with the expression vector pCDNA3.1-CMV-cgFth1-p2A-EGFP under the condition of iron ion-induced ferroptosis in accordance with some embodiments of the present disclosure.

FIG. 16A and FIG. 16B show the experimental results of the HEK293T cell line and the VERO cell line, respectively. The screening performance was evaluated according to the number of fluorescent cells after screening, which showed that increasing the dose of FINO$_2$ in the screening formula would cause significant death of cells transfected with Mock vector (Fth1 was not overexpressed), while the number of surviving fluorescent cells transfected with the vector with the expression of the Fth1 gene and the exogenous gene was significantly increased. It was shown that the vector system could endow cells with resistance to iron ion apoptosis, and maintain exogenous gene expression. In addition, both cell lines exhibited dose-dependent cytotoxic effects, but HEK293T cells were more sensitive to screening formulations and could produce significant screening effects at 1.25 uM FINO$_2$, while VERO cells produced significant screening effects at 5 μM. The experimental results show that the screening system established in the Examples of the present disclosure can also use these two cell lines to screen stable cell lines.

Example 9: Establishment of FTH1 Recombinant Protein Expression Vector for the Production of Recombinant Protein In order to verify that the screening system established in the present disclosure can be applied to the production of recombinant proteins, two expression vectors were respectively constructed based on pBudCE4.1 vector (Invitrogen™) and pCDNA3.1 vector (GenScript) to express a recombinant antibody protein Anti-HER2 IgG1, including pBudCE4.1-CMV-GOI1-SV40-cgFth1-EF1α-GOI2(V2) and pCDNA3.1-CMV-GOI1-furin-p2A-GOI2-IRES-cgFth1 (V3) to express Anti-HER2 IgG1 (h4D5) recombinant monoclonal antibody.

Figure 17A:
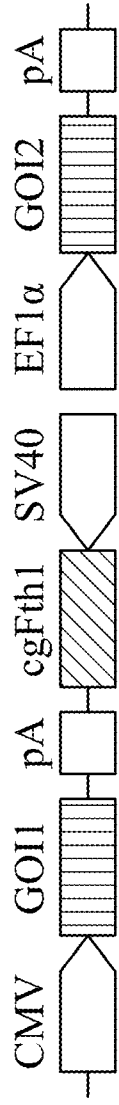
FIG. 17A and FIG. 17B respectively show schematic diagrams of the constructed expression vectors pBudCE4.1-CMV-GOI1-SV40-cgFth1-EF1α-GOI2 and pcDNA3.1-CMV-GOI1-furin-p2A-GOI2-IRES-cgFth1 in accordance with some embodiments of the present disclosure.
Figure 17B:
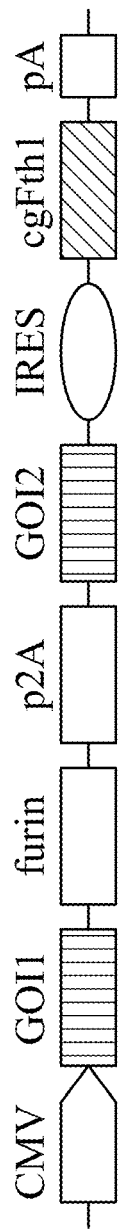

Refer to FIG. 17A and FIG. 17B, which respectively show schematic diagrams of the expression vectors pBudCE4.1-CMV-GOI1-SV40-cgFth1-EF1α-GOI2 and pCDNA3.1-CMV-GOI1-furin-p2A-GOI2-IRES-cgFth1.

As shown in FIG. 17A, the pBudCE4.1-CMV-GOI1-SV40-cgFth1-EF1α-GOI2 expression vector was based on the pBudCE4.1 vector as a backbone, and the CMV promoter, GOI1 gene (Anti-HER2 IgG1 (h4D5) heavy chain variable region), pA terminator, SV40 promoter, cgFth1 gene, EF1a promoter, GOI2 gene (Anti-HER2 IgG1 (h4D5) light chain variable region), and pA terminator were inserted therein. The cgFth1 gene and the Anti-HER2 IgG1(h4D5) gene were driven by two different promoters. The CMV promoter had the nucleotide sequence shown in SEQ ID NO: 7, the GOI1 gene (Anti-HER2 IgG1(h4D5) heavy chain) had the nucleotide sequence shown in SEQ ID NO: 11, the GOI2 gene (Anti-HER2 IgG1(h4D5) light chain) had the nucleic acid sequence shown in SEQ ID NO: 12, the cgFth1 gene had the nucleic acid sequence shown in SEQ ID NO: 4, the EF1α promoter had the nucleic acid sequence shown in SEQ ID NO: 13, and the pA terminator had the nucleic acid sequence shown in SEQ ID NO: 10.

As shown in FIG. 17B, the expression vector pcDNA3.1-CMV-GOI1-furin-p2A-GOI2-IRES-cgFth1 was based on the pcDNA3.1 vector as the backbone, and the CMV promoter, GOI1 gene (Anti-HER2 IgG1 (h4D5) heavy chain variable region), furin gene, p2A gene, GOI2 gene (Anti-HER2 IgG1 (h4D5) light chain variable region), IRES gene, cgFth1 gene, and pA terminator were inserted therein. The IRES gene was located between the cgFth1 gene and the Anti-HER2 IgG1 (h4D5) gene. The CMV promoter had the nucleotide sequence shown in SEQ ID NO: 7, the GOI1 gene (Anti-HER2 IgG1 (h4D5) heavy chain) had the nucleotide sequence shown in SEQ ID NO: 11, and the GOI2 gene (Anti-HER2 IgG1 (h4D5) light chain) had the nucleotide sequence shown in SEQ ID NO: 12, the furin gene had the nucleic acid sequence shown in SEQ ID NO: 14, the p2A peptide had the nucleic acid sequence shown in SEQ ID NO: 8, and the IRES gene had the nucleic acid sequence shown in SEQ ID NO: 15, the cgFth1 gene had the nucleic acid sequence shown in SEQ ID NO: 4, and the pA terminator had the nucleic acid sequence shown in SEQ ID NO: 10.

In order to further verify that FTH1 gene can be expressed by exogenous vector to cause the overexpression of recombinant protein in the cell lines, the expression vectors established in the foregoing Examples were used to transfect the CHOK1 cell line and the HEK293T cell line to promote the overexpression of the FTH1 gene for protein expression analysis.

Specifically, two types of cell lines, CHOK1 and HEK293T, were seeded in 6-well culture plates with 1×10$^5$ cells/well respectively. After 24 hours of adherent culture, the transfection of vectors (pCDNA3.1-CMV-cgFth1-p2A-EGFP, pCDNA3.1-CMV-mFth1-p2A-EGFP, pCDNA3.1-CMV-hFth1-p2A-EGFP, pBudCE4.1-CMV-GOI1-SV40-cgFth1-EF1α-GOI2 and pcDNA3.1-CMV-GOI1-furin-p2A-GOI2-IRES-cgFth1) were carried out with Lipofectamine 3000 (Thermo Fisher Scientific Inc.) to promote the overexpression of FTH1 gene. 72 hours after the DNA transfection of the vectors, cell lysate was prepared with RIPA cell lysate (containing 1× protease inhibitor), and protein was quantified by BCA protein quantification method (Pierce BCA Protein Assay Kit, Thermo Fisher Scientific Inc.), and 8 μg of total protein was taken for protein electrophoresis. In addition, the expression of FTH1 protein was analyzed by Western blotting using anti-FTH1 antibody (ab65080, Abcam Inc.). Furthermore, endogenous protein analysis was performed with GAPDH antibody (ab8245, Abcam Inc.) as a control for the amount of protein. Subsequently, Goat anti-rabbit HRP and Goat anti-mouse HRP were used as secondary antibodies for reaction, and ECL (SuperSignal™ West Pico PLUS Chemiluminescent Substrate, Thermo Fisher Scientific Inc.) was used for color development, and the protein expression level was analyzed with luminescence image analyzer (Fujifilm LAS-4000). The experimental results are shown in FIG. 18A and FIG. 18B.

Figures 18A, 18B:
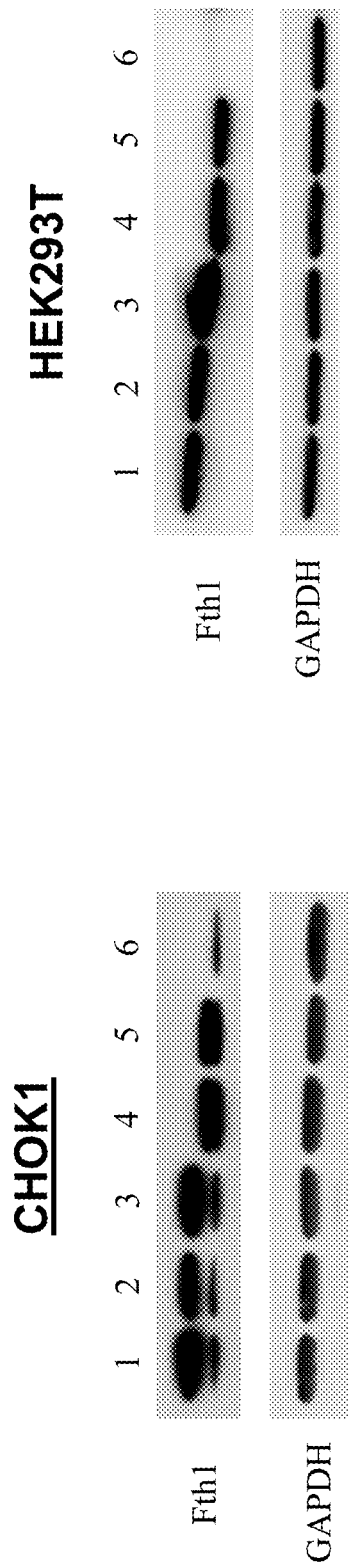
FIG. 18A shows a result of protein expression level of the CHOK1 cell lines analyzed by Western blotting method in accordance with some embodiments of the present disclosure (columns 1 to 6 respectively represent the cell lines transfected with the expression vectors pCDNA3.1-CMV-cgFth1-p2A-EGFP, pCDNA3.1-CMV-hFth1-p2A-EGF, pCDNA3.1-CMV-mFth1-p2A-EGF, pcDNA3.1-CMV-GOI1-furin-p2A-GOI2-IRES-cgFth1, pBudCE4.1-CMV-GOI1-SV40-cgFth1-EF1α-GOI2 and WT).
FIG. 18B shows a result of protein expression level of the HEK293T cell lines analyzed by Western blotting method in accordance with some embodiments of the present disclosure (columns 1 to 6 respectively represent the cell lines transfected with the expression vectors pCDNA3.1-CMV-cgFth1-p2A-EGFP, pCDNA3.1-CMV-hFth1-p2A-EGF, pCDNA3.1-CMV-mFth1-p2A-EGF, pcDNA3.1-CMV-GOI1-furin-p2A-GOI2-IRES-cgFth1, pBudCE4.1-CMV-GOI1-SV40-cgFth1-EF1α-GOI2 and WT).

Referring to FIG. 18A and FIG. 18B, columns 1 to 6 respectively the results of the expression vectors pCDNA3.1-CMV-cgFth1-p2A-EGFP, pCDNA3.1-CMV-hFth1-p2A-EGF, pCDNA3.1-CMV-mFth1-p2A-EGF, pcDNA3.1-CMV-GOI1-furin-p2A-GOI2-IRES-cgFth1, pBudCE4.1-CMV-GOI1-SV40-cgFth1-EF1α-GOI2 and untransfected vector CHOK1 cell line (WT). It can be seen from the above experimental results that both the CHOK1 and HEK293T cell lines can achieve overexpression of FTH1 recombinant protein in the cell lines by means of exogenous vector expression.

Example 10: Production of Recombinant Antibody Using FTH1 Recombinant Protein Expression Vector-1

Next, it was further verified that the expression vector pBudCE4.1-CMV-GOI1-SV40-cgFth1-EF1α-GOI2 and the cell line screening method provided in the Examples of the present disclosure can be used for the production of recombinant proteins. After the aforementioned vector was delivered to CHOK1 cell line, the Chinese hamster FTH1 gene (cgFth1) and Anti-HER2 recombinant antibody gene were used as targets to analyze the mRNA expression and protein expression.

First, $1\times10^6$ of CHOK1 cells (CHOK1, BCRC) were taken and the electroporation (2 mm cuvette, NEPA21 Electroporator) was carried out under the condition of 125V, and 20 µg of the expression vector pBudCE4.1-CMV-GOI1-SV40-cgFth1-EF1α-GOI2 was delivered to the cells. 72 hours after the vector was delivered to the cells, the mRNA and protein expression levels were analyzed using the Chinese hamster Fth1 gene and the Anti-HER2 IgG1 (h4D5) recombinant antibody gene as the targets.

Furthermore, RNA extraction and mRNA qPCR analysis of the FTH1 and the heavy and light chain of Anti-HER2 IgG1 (h4D5) were performed. $1\times10^6$ of cells of a single cell line was extracted with 500 µl TRIsure reagent (Bioline Inc.) for RNA extraction and purified with Direct-zol™ RNA MiniPrep (Zymogen Inc. cat #R2052). After RNA quantification, 200 ng of total RNA, 1 µg of Oligo dT and SuperScript™ IV Reverse Transcriptase were taken for mRNA reverse-transcription to obtain cDNA. The primers for the Anit-Her2 heavy chain transcript, light chain transcript and Chinese hamster FTH1 gene were designed from cDNA using KAPA SYBR® FAST Universal 2xqPCR Master Mix (1 mL) (cat #KK4600, Kapasystems Inc.), for further qPCR analysis. The primer pair of Anti-HER2 IgG1 (h4D5) heavy chain was shown in SEQ ID NOs: 16 and 17, the primer pair of Anti-HER2 IgG1 (h4D5) light chain was shown in SEQ ID NOs: 18 and 19, the primer pair of beta-actin (Cg_Actin-beta) of Chinese hamster, which served as a control group, was shown in SEQ ID NOs: 20 and 21, and the primer pair of Chinese hamster FTH1 (Cg_Fth1) was shown in SEQ ID NOs: 22 and 23.

The quantitative analysis of Anti-HER2 IgG1 (h4D5) recombinant antibody was carried out by ELISA. 1 µg/ml HER2 (HER2-ECD-hFc) recombinant protein was prepared with 0.1 M sodium bicarbonate buffer, and 100 µl of which was added to the 96-well culture plate and placed at 4° C. for coating for 24 hours. Subsequent blocking with Superblock™ (PBS) and washing with PBST buffer at each stage were performed. The cell medium sample was diluted 50 times with StartingBlock blocking solution, and then added to the 96-well culture plate that had been coated with HER2 at 37° C. for 1 hour. After that, it was washed with 200 µl PBST, and the secondary antibody Goat Anti-Human Ig κ chain Antibody (HRP conjugate (Millipore, AP502P) 1:10000 in Superblock™ (PBS)) was added and reacted at 37° C. for 1 hour. After washing with 200 µl of PBST, 100 µl of Ne-blue TMB solution was added for color development, and then the reaction was stopped with 2N HCl, and the assay value was read at OD450 with an ELISA reader.

Figures 19A, 19B, 19C:
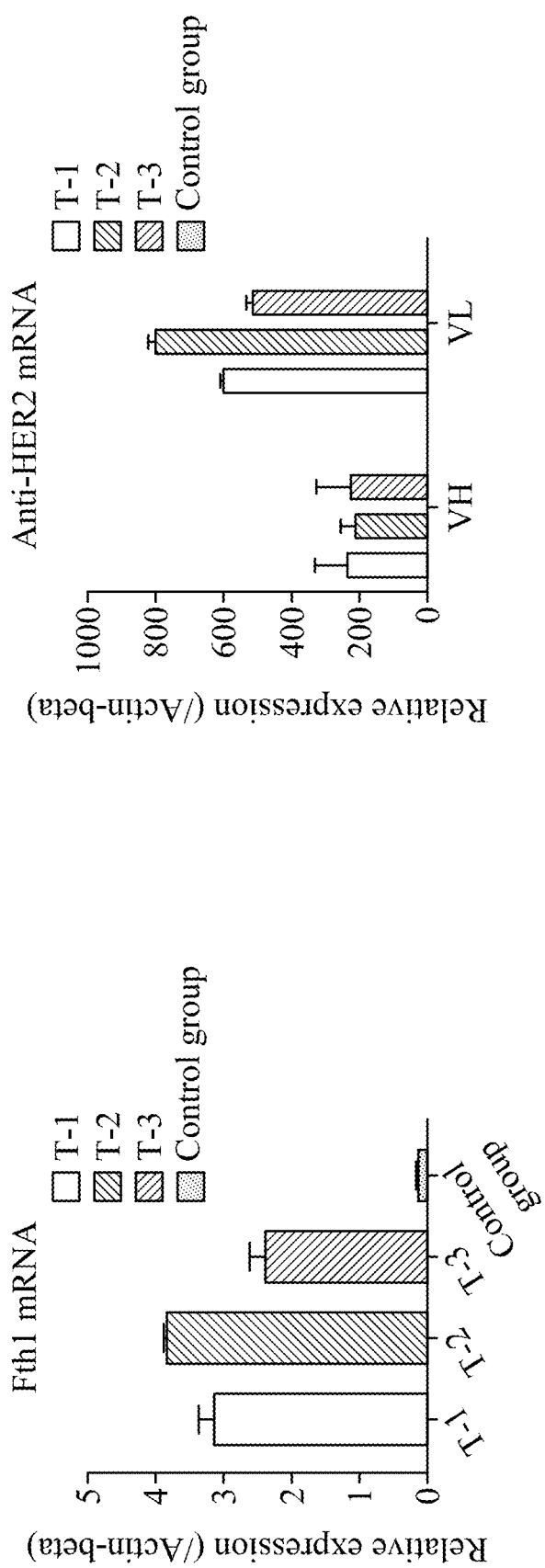
FIG. 19A shows analysis results of the mRNA expression level of FTH1 gene of the CHOK1 cell lines transfected with the expression vector pBudCE4.1-CMV-GOI1-SV40-cgFth1-EF1α-GOI2 in accordance with some embodiments of the present disclosure.
FIG. 19B shows analysis results of the mRNA expression level of the heavy chain (VH) and light chain (VL) of Anti-HER2 IgG1 (h4D5) antibody obtained from the CHOK1 cell line transfected with the expression vector pBudCE4.1-CMV-GOI1-SV40-cgFth1-EF1α-GOI2 in accordance with some embodiments of the present disclosure.
FIG. 19C shows an ELISA analysis result of the expression level of Anti-HER2 IgG1(h4D5) antibody obtained from the CHOK1 cell line transfected with the expression vector pBudCE4.1-CMV-GOI1-SV40-cgFth1-EF1α-GOI2 in accordance with some embodiments of the present disclosure.

The experimental results using pBudCE4.1-CMV-GOI1-SV40-cgFth1-EF1α-GOI2 as the expression vector are shown in FIGS. 19A to 19C. As shown in FIG. 19A, the analysis results of FTH1 mRNA expression showed that in three sets of vector transfection repeatability experiments (T-1, T-2, T-3), the mRNA expression of the FTH1 gene of the CHOK1 cell line in the experimental groups were all significantly higher than that in the control group (about 2.5-4 times). As shown in FIG. 19B, mRNAs of the heavy chain (VH) and light chain (VL) of Anti-HER2 IgG1 (h4D5) antibody were highly expressed (VL: about 200x/control group, VH: about 500-800x/control group). In addition, as shown in FIG. 19C, Anti-HER2 IgG1 (h4D5) antibody could be detected in the cell culture broth by ELISA. It showed that with the design of the pBudCE4.1-CMV-GOI1-SV40-cgFth1-EF1α-GOI2 expression vector using the FTH1 gene as the selection marker, the cell lines with stable expression could be screened out by the cell line screening method provided in the Examples of the present disclosure, and which can be applied to subsequent protein production.

Example 11: Production of Recombinant Antibody Using FTH1 Recombinant Protein Expression Vector-2

Next, it was further verified that the expression vector pcDNA3.1-CMV-GOI1-furin-p2A-GOI2-IRES-cgFth1 and the cell line screening method provided in the Examples of the present disclosure can be used for the production of recombinant proteins. After the aforementioned vector was delivered to CHOK1 cell line, the Chinese hamster FTH1 gene (cgFth1) and Anti-HER2 recombinant antibody gene were used as targets to analyze the mRNA expression and protein expression.

First, $1\times10^6$ of CHOK1 cells (CHOK1, BCRC) were taken and the electroporation (2 mm cuvette, NEPA21 Electroporator) was carried out under the condition of 125V, and 20 µg of the expression vector pcDNA3.1-CMV-GOI1-furin-p2A-GOI2-IRES-cgFth1 was delivered to the cells, and screened with the screening system established in the Examples of the present disclosure. After 8 days of screening, the cells were maintained in the medium formulation containing only iron ions (500 µM ferrous sulfate or 1 mM ferric ammonium citrate) and maintained the gene expression. After screening, the stable cell lines were cultured in suspension with serum-free medium (HyClone CDM4PERMAb medium, 4 mM glutamic acid), and subjected to limiting dilution, and a single cell line derived from a single cell was selected for subsequent analysis of recombinant antibodies.

Next, a small-scale mass production of Anti-HER2 IgG1 (h4D5) recombinant antibody was carried out. The single cell line was seeded in 4.5 ml of serum-free medium (HyClone CDM4PERMAb medium, 4 mM glutamic acid) with $3\times10^5$ cells/ml, and was subjected to suspension culture in 50 ml of TubeSpin® Bioreactor (225 rpm, 37° C., 5% $CO_2$). After 4 days of culture, the cells were removed by centrifugation and the cell culture broth was collected for enzyme-linked immunosorbent assay (ELISA) to analyze the concentration of antibody. Furthermore, the antibody was subsequently purified using MabSelect SuRe™ LX.

Furthermore, RNA extraction and mRNA qPCR analysis of the FTH1 and the heavy and light chain of Anti-HER2 IgG1 (h4D5) were performed. $1\times10^6$ cells of a single cell line was extracted with 500 µl TRIsure reagent (Bioline Inc.) for RNA extraction and purified with Direct-zol™ RNA MiniPrep (Zymogen Inc. cat #R2052). After RNA quantification, 200 ng of total RNA, 1 µg of Oligo dT and SuperScript™ IV Reverse Transcriptase were taken for mRNA reverse-transcription to obtain cDNA. The primers for the Anit-Her2 heavy chain transcript, light chain transcript and Chinese hamster FTH1 gene were designed from cDNA using KAPA SYBR® FAST Universal 2xqPCR Master Mix (1 mL) (cat #KK4600, Kapasystems Inc.), for further qPCR analysis. The primer pair of Anti-HER2 IgG1 (h4D5) heavy chain was shown in SEQ ID NOs: 16 and 17, the primer pair of Anti-HER2 IgG1 (h4D5) light chain was shown in SEQ ID NOs: 18 and 19, the primer pair of beta-actin (Cg_Actin-beta) of Chinese hamster, which served as a control group, was shown in SEQ ID NOs: 20 and 21, and the primer pair of Chinese hamster FTH1 (Cg_Fth1) was shown in SEQ ID NOs: 22 and 23.

The quantitative analysis of Anti-HER2 IgG1 (h4D5) recombinant antibody was carried out by ELISA. 1 µg/ml HER2 (HER2-ECD-hFc) recombinant protein was prepared with 0.1 M sodium bicarbonate buffer, and 100 µl of which was added to the 96-well culture plate and placed at 4° C. for coating for 24 hours. Subsequent blocking with Superblock™ (PBS) and washing with PBST buffer at each stage were performed. The cell medium sample was diluted 50 times with StartingBlock blocking solution, and then added to the 96-well culture plate that had been coated with HER2 at 37° C. for 1 hour. After that, it was washed with 200 µl PBST, and the secondary antibody Goat Anti-Human Ig κ chain Antibody (HRP conjugate (Millipore, AP502P) 1:10000 in Superblock™ (PBS)) was added and reacted at 37° C. for 1 hour. After washing with 200 µl of PBST, 100 µl of Ne-blue TMB solution was added for color development, and then the reaction was stopped with 2N HCl, and the assay value was read at OD450 with an ELISA reader.

The experimental results using pcDNA3.1-CMV-GOI1-furin-p2A-GOI2-IRES-cgFth1 as the expression vector are shown in FIGS. 20A to 20D. As shown in FIG. 20A and FIG. 20B, for the four groups of clones (clone-3, clone-4, clone-8, clone-11), both the mRNAs of the heavy chain (VH) and light chain (VL) of Anti-HER2 IgG1 (h4D5) antibody were highly expressed. In addition, as shown in FIG. 20C, the analysis results of the expression of FTH1 mRNA showed that the mRNA expression levels of FTH1 gene in four groups of CHOK1 cell line clones (clone-3, clone-4, clone-8, clone-11) were significantly higher than those of the control group. In addition, as shown in FIG. 20D, Anti-HER2 IgG1 (h4D5) antibody could be detected in the cell culture broth by ELISA, and the expression level of clone-8 (cell strain C8) was relatively high. It showed that with the design of the pcDNA3.1-CMV-GOI1-furin-p2A-GOI2-IRES-cgFth1 expression vector using the FTH1 gene as the selection marker, the cell lines with stable expression could be screened out by the cell line screening method provided in the Examples of the present disclosure, and which can be applied to subsequent protein production.

Example 12: Conformation Verification of Recombinant Antibodies Produced Using FTH1 Recombinant Protein Expression Vector In order to verify that the conformation of the Anti-HER2 antibody (IgG antibody) expressed by the expression vector is correct, protein electrophoresis was used for analysis.

The Anti-HER2 IgG1 (h4D5) recombinant protein that was produced by cell line C8 screened in Example 11 was analyzed by SDS-PAGE protein electrophoresis, and Anti-HER2 IgG1 (h4D5) recombinant protein produced by a self-constructed vector (pCMV-GOI1-EF1α-GOI2-SV40-Hygromycin B phosphotransferase) using Hygromycin B as a selection marker was used as a standard for comparison. 1.5 µg of purified recombinant protein samples were taken, and 100 µM DTT reduced and non-reduced proteins were used for SDS gel electrophoresis (NuPAGE™ 4-12%, Bis-Tris, Thermo Fisher Scientific Inc.). The gel electrophoresis analysis was performed with MOPS buffer at 200V voltage, and finally staining analysis was conducted with protein gel stain (InstantBlue™ Ultrafast Protein Stain, Sigma-Aldrich), and the correctness of the produced recombinant antibodies was evaluated by protein molecular weight. The experimental results are shown in FIG. 21.

Figure 21:
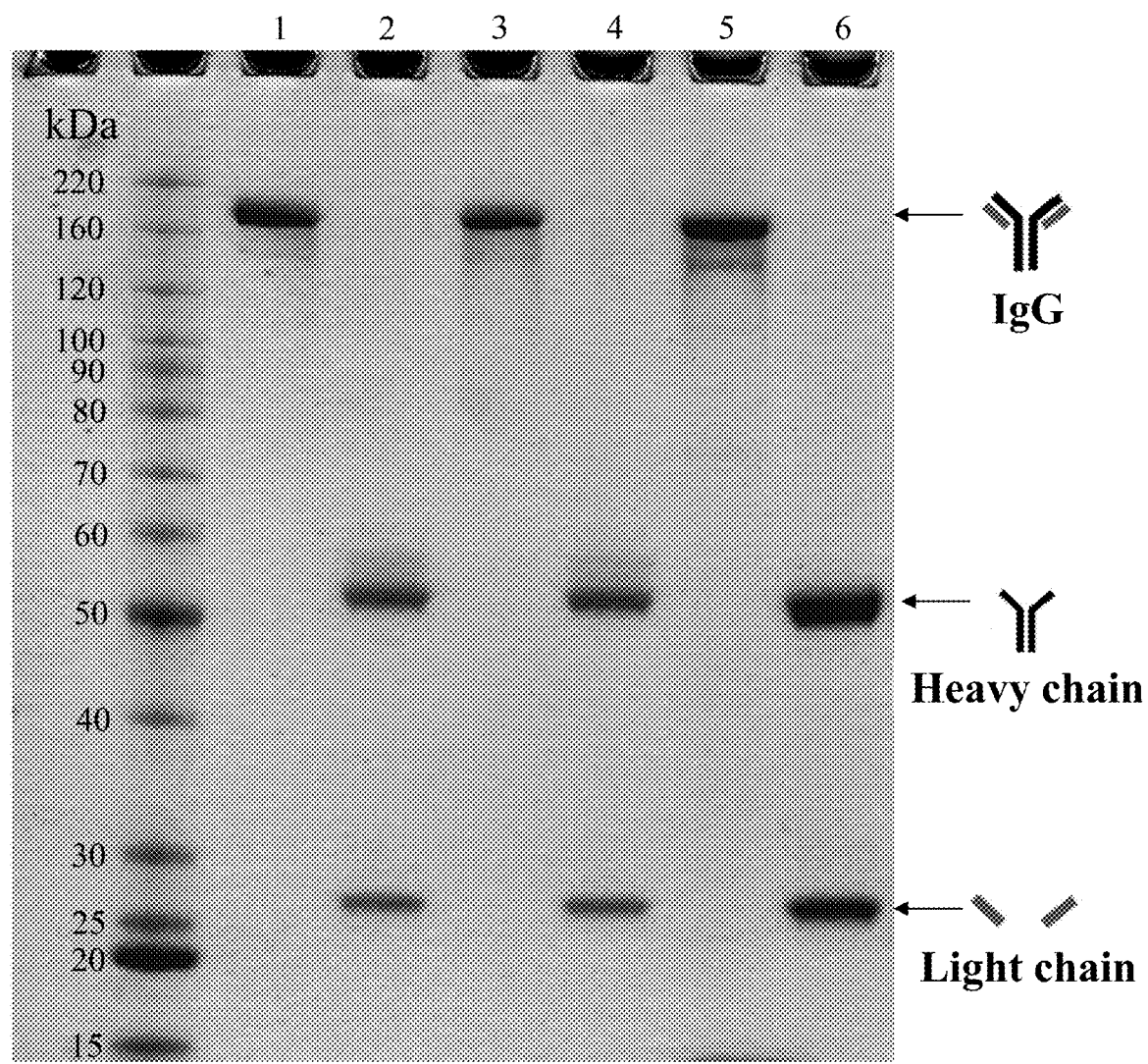
FIG. 21 shows an analysis result of the conformation of Anti-HER2 IgG1 (h4D5) recombinant protein by SDS-PAGE protein electrophoresis in accordance with some embodiments of the present disclosure (columns 1 to 6 respectively represent Anti-HER2 IgG1 recombinant protein_unreduced form, Anti-HER2 IgG1 recombinant protein_reduced form, Anti-HER2 IgG1 recombinant protein_FAC+unreduced form, Anti-HER2 IgG1 recombinant protein_FAC+reduced form, Anti-HER2 IgG standard_unreduced form, and Anti-HER2 IgG1 purified protein standard_reduced form).

Referring to FIG. 21, columns 1 to 6 respectively represent the results of Anti-HER2 IgG1 recombinant protein_unreduced form, Anti-HER2 IgG1 recombinant protein_reduced form, Anti-HER2 IgG1 recombinant protein_FAC+unreduced form, Anti-HER2 IgG1 recombinant protein_FAC+reduced form, Anti-HER2 IgG standard_unreduced form, and Anti-HER2 IgG1 standard_reduced form, wherein the protein ladder marker used was: BenchMark Protein Ladder SDS page, and 1.5 µg of recombinant protein was added to each column.

As shown in FIG. 21, compared with the Anti-HER2 IgG1 (h4D5) protein standard, the cell line C8 obtained by the expression vector and the screening system provided by the present disclosure could express complete IgG1 antibody and had the correct heavy chain (VH) and light chain (VL) molecular weights when the protein was in the unreduced form and the reduced form, or when the medium contained 250 µM ferric ammonium citrate (FAC). It showed that the cell line obtained by the cell line screening method provided in the Examples of the present disclosure can produce the correct recombinant antibody protein.

Example 13: Functional Analysis of Recombinant Antibodies Produced Using FTH1 Recombinant Protein Expression Vectors In order to verify that the Anti-HER2 IgG1 (h4D5) antibody produced by the expression vector is a functional antibody, an analysis test was performed with antibody-dependent cell-mediated cytotoxicity (ADCC).

Jurkat-hFcγRIIIa-NFAT gene transgenic cells was used as effector cells and SKBR3 breast cancer cells rich in HER2 antigen was used as target cells in ADCC biological activity reporter gene detection system (Promega, #G9790). In addition, the ADCC biological activity detection of anti-HER2 monoclonal antibody, Anti-HER2 IgG1, was carried out by luminescent luciferase detection system (BioGlo™ Luciferase Assay system).

For the cell line C8 obtained by screening in Example 11 (the expression vector pcDNA3.1-CMV-GOI1-furin-p2A-GOI2-IRES-cgFth1 (V3) was used), the recombinant antibodies produced under the conditions of adding iron ions (250 Anti-HER2 IgG1_V3_C8-FAC-250 µM FAC+) and without adding iron ions (Anti-HER2 IgG1_V3_C8) during the screening process were tested. The recombinant antibody (Anti-HER2 IgG1_V2) produced by the expression vector pBudCE4.1-CMV-GOI1-cgFth1-SV40/EF1α-GOI2 (V2) was also evaluated.

First, 100 µl of SKBR3 cells with a cell density of $10^5$/ml were added to the 96-well culture plate, placed at 37° C. for overnight culture to allow the cells to adhere and grow, the supernatant was removed the next day, and 25 µl of serially diluted recombinant antibodies prepared in GOIMI-1640 medium containing 0.5% fetal bovine serum were added. Next, 25 µl of lurkat-hFcγRIIIa-NFAT effector cells with a cell density of $6 \times 10^6$/ml were added. After 24 hours of reaction, 75 µl of Bio-Glo™ Luciferase Assay Buffer was added for the reaction, and the luminescence signal was read on the GloMax® Navigator Microplate Luminometer to measure the ADCC effect of the antibody Anti-HER2 IgG1 (h4D5). The experimental results are shown in FIG. 22.

Figure 22:
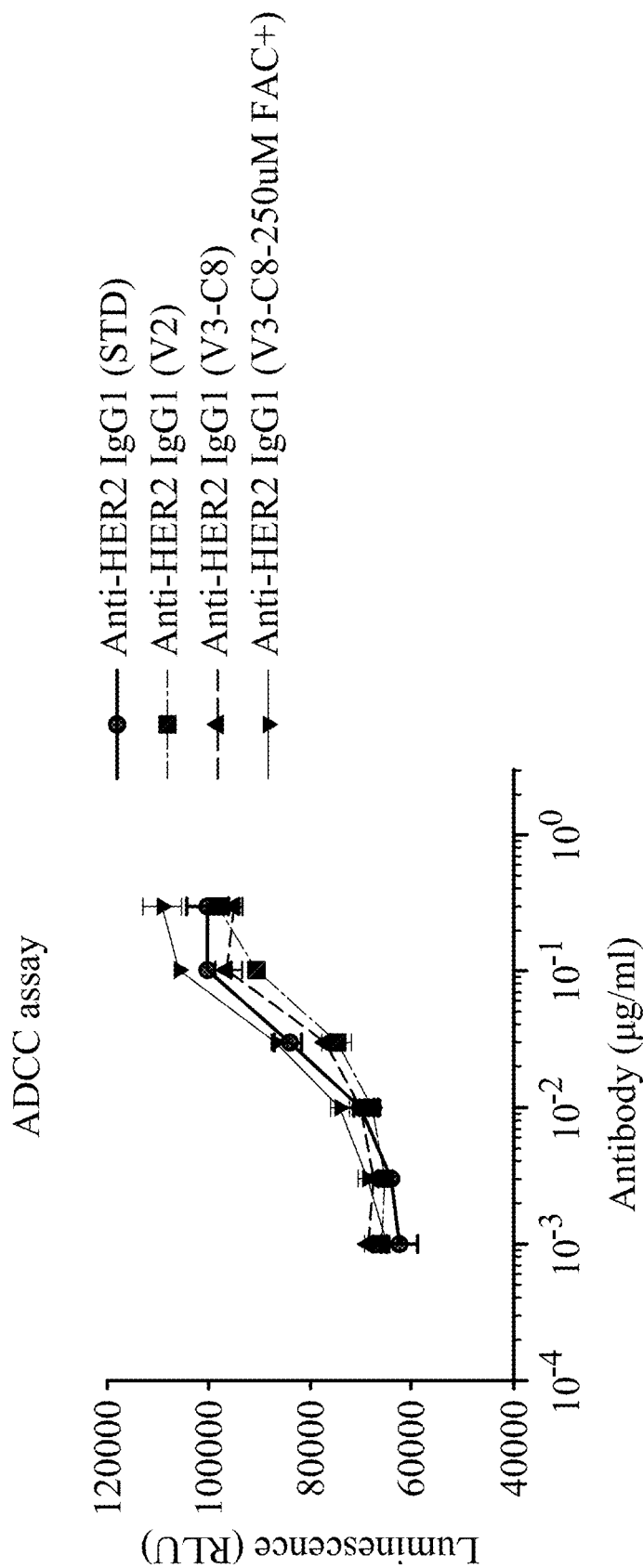
FIG. 22 shows results of the ADCC biological activity assay of Anti-HER2 IgG1 (h4D5) produced in accordance with some embodiments of the present disclosure.

As shown in FIG. 22, compared with the Anti-HER2 IgG1 (h4D5) recombinant antibody protein validated after purification, the recombinant antibodies obtained using the expression vectors pcDNA3.1-CMV-GOI1-furin-p2A-GOI2-IRES-cgFth1 (V3) and pBudCE4.1-CMV-GOI1-SV40-cgFth1-EF1α-GOI2(V2) could obviously induce ADCC. In addition, the group in which iron ions were added to the screening process (Anti-HER2 IgG1_V3_C8-FAC-250 µM FAC+) also had the same effect, indicating that the addition of iron ions did not affect the functionality of the recombinant antibody.

Although some embodiments of the present disclosure and their advantages have been described as above, it should be understood that various changes, substitutions and alterations can be made herein without departing from the spirit and scope of the disclosure as defined by the appended claims. In addition, each claim constitutes an individual embodiment, and the claimed scope of the present disclosure also includes the combinations of the claims and embodiments. The scope of protection of the present disclosure is subject to the definition of the scope of the appended claims.

What is claimed is:

1. A method for screening and selecting mammalian host cells expressing a target protein, comprising:
   (a) providing an expression vector comprising a promoter, a gene encoding a target protein and a Ferritin Heavy Chain 1 (FTH1) gene, wherein the FTH1 gene is used as a selection marker;
   (b) transfecting the mammalian host cells with the expression vector;
   (c) culturing the transfected mammalian host cells of step (b) in a culture medium;
   (d) adding 100 μM to 1.5 mM of iron ions and 0.5 μM to 2 mM of a ferroptosis inducer to the culture medium of step (c); and
   (e) screening and selecting the surviving mammalian host cells comprising the expression vector to obtain the mammalian host cells expressing the target protein.

2. The method of claim 1, wherein the gene encoding the target protein and the FTH1 gene are driven by the same promoter.

3. The method of claim 1, wherein the gene encoding the target protein and the FTH1 gene are driven by different promoters.

4. The method of claim 1, wherein the mammalian host cell is selected from the group consisting of a CHO cell, a HEK293 cell, a Hela cell, a VERO cell, and a NS0 cell.

5. The method of claim 1, wherein the mammalian host cells are FTH1 gene-knockout cells.

6. The method of claim 1, wherein the step of screening and selecting the mammalian host cells further comprises adding a fatty acid to the medium of step (d).

7. The method of claim 6, wherein the fatty acid is added at a concentration of 50 μM to 500 μM.

8. The method of claim 1, wherein the target protein comprises a recombinant protein.

9. The method of claim 8, wherein the recombinant protein comprises an antibody.

10. The method of claim 1, further comprising:
   (f) continuously the surviving and selected mammalian host cells expressing the target protein of step (e) in the culture medium containing the 100 µM to 1.5 mM of the iron ions to grow the surviving and selected mammalian host cells and maintain the expression of the gene encoding the target protein.

* * * * *

SEQUENCE LISTING

```
<160> NUMBER OF SEQ ID NOS: 23

<210> SEQ ID NO 1
<211> LENGTH: 186
<212> TYPE: PRT
<213> ORGANISM: Cricetulus griseus

<400> SEQUENCE: 1

Met Thr Thr Thr Ala Leu Thr Thr Ala Ser Pro Ser Gln Val Arg Gln
1               5                   10                  15

Asn Tyr His Gln Asp Ser Glu Ala Ala Ile Asn Arg Gln Ile Asn Leu
            20                  25                  30

Glu Leu Tyr Ala Ser Tyr Val Tyr Leu Ser Met Ser Cys Tyr Phe Asp
        35                  40                  45

Arg Asp Asp Val Ala Leu Lys Asn Phe Ala Lys Tyr Phe Leu His Gln
    50                  55                  60

Ser His Glu Glu Arg Glu His Ala Glu Lys Leu Met Lys Leu Gln Asn
65                  70                  75                  80

Gln Arg Gly Gly Arg Ile Phe Leu Gln Asp Ile Lys Lys Pro Asp Arg
                85                  90                  95

Asp Asp Trp Glu Ser Gly Leu Asn Ala Met Glu Cys Ala Leu His Leu
            100                 105                 110

Glu Lys Ser Val Asn Gln Ser Leu Leu Glu Leu His Lys Leu Ala Thr
        115                 120                 125

Asp Lys Asn Asp Pro His Leu Cys Asp Phe Ile Glu Thr His Tyr Leu
    130                 135                 140

Asn Glu Gln Val Lys Ser Ile Lys Glu Leu Gly Asp His Val Thr Asn
145                 150                 155                 160

Leu Arg Lys Met Gly Ala Pro Glu Ala Gly Met Ala Glu Tyr Leu Phe
                165                 170                 175

Asp Lys His Thr Leu Gly His Ser Glu Ser
            180                 185

<210> SEQ ID NO 2
<211> LENGTH: 184
<212> TYPE: PRT
<213> ORGANISM: Mus musculus

<400> SEQUENCE: 2

Met Thr Thr Ala Ser Pro Ser Gln Val Arg Gln Asn Tyr His Gln Asp
1               5                   10                  15

Ala Glu Ala Ala Ile Asn Arg Gln Ile Asn Leu Glu Leu Tyr Ala Ser
            20                  25                  30

Tyr Val Tyr Leu Ser Met Ser Cys Tyr Phe Asp Arg Asp Asp Val Ala
        35                  40                  45

Leu Lys Asn Phe Ala Lys Tyr Phe Leu His Gln Ser His Glu Glu Arg
    50                  55                  60
```

```
Glu His Ala Glu Lys Leu Met Lys Leu Gln Asn Gln Arg Gly Gly Arg
 65                  70                  75                  80

Ile Phe Leu Gln Asp Ile Lys Lys Pro Asp Arg Asp Asp Trp Glu Ser
                 85                  90                  95

Gly Leu Asn Ala Met Glu Cys Ala Leu His Leu Glu Lys Ser Val Asn
            100                 105                 110

Gln Ser Leu Leu Glu Leu His Lys Leu Ala Thr Asp Lys Asn Asp Pro
        115                 120                 125

His Leu Cys Asp Phe Ile Glu Thr Tyr Tyr Leu Ser Glu Gln Val Lys
    130                 135                 140

Ser Ile Lys Glu Leu Gly Asp His Val Thr Asn Leu Arg Lys Met Gly
145                 150                 155                 160

Ala Pro Glu Ala Gly Met Ala Glu Tyr Leu Phe Asp Lys His Thr Leu
                165                 170                 175

Gly His Gly Asp Glu Ser Ser Arg
            180
```

<210> SEQ ID NO 3
<211> LENGTH: 184
<212> TYPE: PRT
<213> ORGANISM: Homo sapiens

<400> SEQUENCE: 3

```
Met Thr Thr Ala Ser Thr Ser Gln Val Arg Gln Asn Tyr His Gln Asp
  1               5                  10                  15

Ser Glu Ala Ala Ile Asn Arg Gln Ile Asn Leu Glu Leu Tyr Ala Ser
                 20                  25                  30

Tyr Val Tyr Leu Ser Met Ser Tyr Tyr Phe Asp Arg Asp Asp Val Ala
             35                  40                  45

Leu Lys Asn Phe Ala Lys Tyr Phe Leu His Gln Ser His Glu Glu Arg
 50                  55                  60

Glu His Ala Glu Lys Leu Met Lys Leu Gln Asn Gln Arg Gly Gly Arg
 65                  70                  75                  80

Ile Phe Leu Gln Asp Ile Lys Lys Pro Asp Cys Asp Asp Trp Glu Ser
                 85                  90                  95

Gly Leu Asn Ala Met Glu Cys Ala Leu His Leu Glu Lys Asn Val Asn
            100                 105                 110

Gln Ser Leu Leu Glu Leu His Lys Leu Ala Thr Asp Lys Asn Asp Pro
        115                 120                 125

His Leu Cys Asp Phe Ile Glu Thr His Tyr Leu Asn Glu Gln Val Lys
    130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Asn Glu Ser Ser
            180
```

<210> SEQ ID NO 4
<211> LENGTH: 559
<212> TYPE: DNA
<213> ORGANISM: Cricetulus griseus

<400> SEQUENCE: 4

```
atgaccacca ccgccctgac caccgcgtct ccctcgcagg tgcgccagaa ctaccaccag    60
```

```
gactcggagg ctgccatcaa ccgccagatc aacctggaac tgtacgcctc ctacgtctat    120
ctgtctatgt cttgctactt tgaccgggat gatgtggctc tgaagaactt tgccaaatac    180
tttctccacc aatctcatga ggagagggaa cacgctgaga aactgatgaa gctgcagaac    240
caacgaggtg gccgaatctt cctgcaggat atcaagaaac cagaccgtga tgactgggag    300
agtgggctga acgcaatgga gtgtgcactg cacttggaaa agagtgtgaa tcagtcacta    360
ctggaactgc acaaactggc tactgacaaa aatgaccccc atttgtgtga cttcattgag    420
acccattacc tgaatgagca ggtgaaatcc atcaaagagc tgggtgacca cgtgaccaac    480
ttgcgcaaga tgggagcccc tgaagctggc atggcagaat atctctttga caagcacacc    540
ctgggacata gtgagagct                                                  559

<210> SEQ ID NO 5
<211> LENGTH: 552
<212> TYPE: DNA
<213> ORGANISM: Mus musculus

<400> SEQUENCE: 5
atgaccaccg cgtctccctc gcaagtgcgc cagaactacc accaggacgc ggaggctgcc     60
atcaaccgcc agatcaacct ggagttgtat gcctcctacg tctatctgtc tatgtcttgt    120
tattttgacc gagatgatgt ggctctgaag aactttgcca atactttct ccaccaatct     180 catgaggaga gggagcatgc cgagaaactg atgaagctgc agaaccagcg aggtggccga    240
atcttcctgc aggatataaa gaaaccagac cgtgatgact gggagagcgg gctgaatgca    300
atggagtgtg cactgcactt ggaaaagagt gtgaatcagt cactactgga actgcacaaa    360
ctggctactg acaagaatga tcccccactta tgtgacttca ttgagacgta ttatctgagt    420
gaacaggtga atccattaa agaactgggt gaccacgtga ccaacttacg caagatgggt    480
gcccctgaag ctggcatggc agaatatctc tttgacaagc acaccctggg cacggtgat    540 gagagctcta ga                                                        552

<210> SEQ ID NO 6
<211> LENGTH: 554
<212> TYPE: DNA
<213> ORGANISM: Homo sapiens

<400> SEQUENCE: 6
atgacgaccg cgtccacctc gcaggtgcgc cagaactacc accaggactc agaggccgcc     60
atcaaccgcc agatcaacct ggagctctac gcctcctacg tttacctgtc catgtcttac    120
tactttgacc gcgatgatgt ggcttttgaag aactttgcca atactttct tcaccaatct    180 catgaggaga gggaacatgc tgagaaactg atgaagctgc agaaccaacg aggtggccga    240
atcttccttc aggatatcaa gaaaccagac tgtgatgact gggagagcgg gctgaatgca    300
atggagtgtg cattacattt ggaaaaaaat gtgaatcagt cactactgga actgcacaaa    360
ctggccactg acaaaaatga ccccattttg tgtgacttca ttgagacaca ttacctgaat    420
gagcaggtga aagccatcaa agaattgggt gaccacgtga ccaacttgcg caagatggga    480
gcgcccgaat ctggcttggc ggaatatctc tttgacaagc acaccctggg agacagtgat    540
aatgaaagct ctag                                                      554

<210> SEQ ID NO 7
<211> LENGTH: 584
<212> TYPE: DNA
<213> ORGANISM: Artificial Sequence
```

```
<220> FEATURE:
<223> OTHER INFORMATION: CMV promoter

<400> SEQUENCE: 7
gacattgatt attgactagt tattaatagt aatcaattac ggggtcatta gttcatagcc      60
catatatgga gttccgcgtt acataactta cggtaaatgg cccgcctggc tgaccgccca     120
acgacccccg cccattgacg tcaataatga cgtatgttcc catagtaacg ccaataggga     180
ctttccattg acgtcaatgg gtggagtatt tacggtaaac tgcccacttg gcagtacatc     240
aagtgtatca tatgccaagt acgccccta ttgacgtcaa tgacggtaaa tggcccgcct     300
ggcattatgc ccagtacatg accttatggg actttcctac ttggcagtac atctacgtat     360
tagtcatcgc tattaccatg gtgatgcggt tttggcagta catcaatggg cgtggatagc     420
ggtttgactc acggggattt ccaagtctcc accccattga cgtcaatggg agtttgtttt     480
ggcaccaaaa tcaacgggac tttccaaaat gtcgtaacaa ctccgcccca ttgacgcaaa     540
tgggcggtag gcgtgtacgg tgggaggtct atataagcag agct                      584

<210> SEQ ID NO 8
<211> LENGTH: 66
<212> TYPE: DNA
<213> ORGANISM: Artificial Sequence
<220> FEATURE:
<223> OTHER INFORMATION: p2A peptide

<400> SEQUENCE: 8
ggaagcggag ctactaactt cagcctgctg aagcaggctg agacgtgga ggagaaccct       60 ggacct                                                                 66

<210> SEQ ID NO 9
<211> LENGTH: 717
<212> TYPE: DNA
<213> ORGANISM: Artificial Sequence
<220> FEATURE:
<223> OTHER INFORMATION: EGFP protein

<400> SEQUENCE: 9
atgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg gcccaccctc     180
gtgaccaccc tgacctacgg cgtgcagtgc ttcagccgct accccgacca catgaagcag     240
cacgacttct tcaagtccgc catgcccgaa ggctacgtcc aggagcgcac catcttcttc     300
aaggacgacg gcaactacaa gacccgcgcc gaggtgaagt tcgagggcga caccctggtg     360
aaccgcatcg agctgaaggg catcgacttc aaggaggacg gcaacatcct ggggcacaag     420
ctggagtaca actacaacag ccacaacgtc tatatcatgg ccgacaagca gaagaacggc     480
atcaaggtga acttcaagat ccgccacaac atcgaggacg gcagcgtgca gctcgccgac     540
cactaccagc agaacacccc catcggcgac ggccccgtgc tgctgcccga caaccactac     600
ctgagcaccc agtccgccct gagcaaagac cccaacgaga gcgcgatca catggtcctg     660 ctggagttcg tgaccgccgc cgggatcact cacggcatgg acgagctgta caagtaa        717

<210> SEQ ID NO 10
<211> LENGTH: 225
<212> TYPE: DNA
<213> ORGANISM: Artificial Sequence
<220> FEATURE:
```

<223> OTHER INFORMATION: polyA terminator

<400> SEQUENCE: 10

| | | |
|---|---|---|
| ctgtgccttc tagttgccag ccatctgttg tttgcccctc ccccgtgcct tccttgaccc | 60 |
| tggaaggtgc cactcccact gtcctttcct aataaaatga ggaaattgca tcgcattgtc | 120 |
| tgagtaggtg tcattctatt ctgggggggtg gggtggggca ggacagcaag ggggaggatt | 180 |
| gggaagacaa tagcaggcat gctggggatg cggtgggctc tatgg | 225 |

<210> SEQ ID NO 11
<211> LENGTH: 1413
<212> TYPE: DNA
<213> ORGANISM: Artificial Sequence
<220> FEATURE:
<223> OTHER INFORMATION: Anti-HER2 IgG1 antibody VH

<400> SEQUENCE: 11

| | |
|---|---|
| atggagacag acacactcct gctatgggta ctgctgctct ggttccaggt tccactggt | 60 |
| gatatccagc tgcaggagag cggcggcggt ctggtgcagc ctggcggcag cctgaggctg | 120 |
| agctgcgccg ccagcggctt caacatcaag gacacctaca tccactgggt gaggcaggcc | 180 |
| cctggcaagg gcctggagtg ggtggccagg atctacccta ccaacggcta caccaggtac | 240 |
| gccgacagcg tgaagggcag gttcaccatc agcgccgaca ccagcaagaa caccgcctac | 300 |
| ctgcagatga acagcctgag ggccgaggac accgccgtgt actactgcag caggtggggc | 360 |
| ggcgacggct tctacgccat ggacgtgtgg ggccagggca ccctggtgac cgtgagcagc | 420 |
| gctagcacca agggcccatc ggtcttcccc ctggcaccct cctccaagag cacctctggg | 480 |
| ggcacagcgg ccctgggctg cctggtcaag gactacttcc ccgaaccggt gacggtgtcg | 540 |
| tggaactcag gcgccctgac cagcggcgtg cacaccttcc cggctgtcct acagtcctca | 600 |
| ggactctact ccctcagcag cgtggtgacc gtgccctcca gcagcttggg cacccagacc | 660 |
| tacatctgca acgtgaatca caagcccagc aacaccaagg tggacaagaa agttgagccc | 720 |
| aaatcttgtg acaaaactca cacatgccca ccgtgcccag cacctgaact cctggggga | 780 |
| ccgtcagtct tcctcttccc cccaaaaccc aaggacaccc tcatgatctc ccggaccct | 840 |
| gaggtcacat gcgtggtggt ggacgtgagc cacgaagacc ctgaggtcaa gttcaactgg | 900 |
| tacgtggacg gcgtggaggt gcataatgcc aagacaaagc cgcggaggga gcagtacaac | 960 |
| agcacgtacc gtgtggtcag cgtcctcacc gtcctgcacc aggactggct gaatggcaag | 1020 |
| gagtacaagt gcaaggtctc caacaaagcc ctcccagccc ccatcgagaa aaccatctcc | 1080 |
| aaagccaaag gcagccccg agaaccacag gtgtacaccc tgcccccatc ccgggatgag | 1140 |
| ctgaccaaga accaggtcag cctgacctgc ctggtcaaag gcttctatcc cagcgacatc | 1200 |
| gccgtggagt gggagagcaa tgggcagccg gagaacaact acaagaccac gcctcccgtg | 1260 |
| ctggactccg acggctcctt cttcctctac agcaagctca ccgtggacaa gagcaggtgg | 1320 |
| cagcagggga acgtcttctc atgctccgtg atgcatgagg ctctgcacaa ccactacacg | 1380 |
| cagaagagcc tctccctgtc tccgggtaaa tga | 1413 |

<210> SEQ ID NO 12
<211> LENGTH: 705
<212> TYPE: DNA
<213> ORGANISM: Artificial Sequence
<220> FEATURE:
<223> OTHER INFORMATION: Anti-HER2 IgG1 antibody VL

<400> SEQUENCE: 12

```
atggagacag acacactcct gctatgggta ctgctgctct gggttccagg ttccactggt    60
gatatccaga tgacccagag ccctagcagc ctgagcgcca gcgtgggcga cagggtgacc   120
atcacctgca gggccagcca ggacgtgaac accgccgtgg cctggtacca gcagaagcct   180
ggcaaggccc ctaagctgct gatctacagc gccagcttcc tggagagcgg cgtgcctagc   240
aggtttagcg gcagcaggag cggcaccgac ttcaccctga ccatcagcag cctgcagcct   300
gaggacttcg ccacctacta ctgccagcag cactacacca cccctcctac cttcggccag   360
ggcaccaagg tggagatcaa gcgtacggtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg ataacgccc tccaatcggg taactcccag   540
gagagtgtca cagagcagga cagcaaggac agcacctaca gcctcagcag cacccctgacg   600 ctgagcaaag cagactacga gaaacacaaa gtctacgcct gcgaagtcac ccatcagggc   660
ctgagctcgc ccgtcacaaa gagcttcaac aggggagagt gttag                   705
```

<210> SEQ ID NO 13
<211> LENGTH: 1163
<212> TYPE: DNA
<213> ORGANISM: Artificial Sequence
<220> FEATURE:
<223> OTHER INFORMATION: EF-1alpha promoter

<400> SEQUENCE: 13

```
ggctccggtg cccgtcagtg ggcagagcgc acatcgccca cagtccccga gaagttgggg    60
ggaggggtcg gcaattgaac cggtgcctag agaaggtggc gcggggtaaa ctgggaaagt   120
gatgtcgtgt actggctccg ccttttttccc gagggtgggg gagaaccgta tataagtgca   180
gtagtcgccg tgaacgttct ttttcgcaac gggtttgccg ccagaacaca ggtaagtgcc   240
gtgtgtggtt cccgcgggcc tggcctcttt acgggttatg gcccttgcgt gccttgaatt   300
acttccacct ggctccagta cgtgattctt gatcccgagc tggagccagg ggcgggcctt   360
gcgctttagg agccccttcg cctcgtgctt gagttgaggc ctggcctggg cgctggggcc   420
gccgcgtgcg aatctggtgg caccttcgcg cctgtctcgc tgctttcgat aagtctctag   480
ccatttaaaa tttttgatga cctgctgcga cgctttttt ctggcaagat agtcttgtaa   540
atgcgggcca ggatctgcac actggtattt cggttttttgg gcccgcggcc ggcgacgggg   600
cccgtgcgtc ccagcgcaca tgttcggcga ggcggggcct gcgagcgcgg ccaccgagaa   660
tcggacgggg gtagtctcaa gctggccggc ctgtctggt gcctggcctc gcgccgccgt   720
gtatcgcccc gccctgggcg gcaaggctgg cccggtcggc accagttgcg tgagcggaaa   780
gatggccgct tccggccct gctccagggg gctcaaaatg gaggacgcgg cgctcggag    840 agcgggcggg tgagtcaccc acacaaagga aaagggcctt ccgtcctca gccgtcgctt    900 catgtgactc cacggagtac cgggcgccgt ccagcaccct cgattagttc tggagctttt   960
ggagtacgtc gtctttaggt tggggggagg ggttttatgc gatggagttt ccccacactg  1020
agtgggtgga gactgaagtt aggccagctt ggcacttgat gtaattctcg ttggaatttg  1080 cccttttttga gtttggatct tggttcattc tcaagcctca gacagtggtt caaagttttt  1140
ttcttccatt tcaggtgtcg tga                                          1163
```

<210> SEQ ID NO 14
<211> LENGTH: 12
<212> TYPE: DNA

```
<213> ORGANISM: Artificial Sequence
<220> FEATURE:
<223> OTHER INFORMATION: furin protease

<400> SEQUENCE: 14
cgtcgtaaac gt                                                              12

<210> SEQ ID NO 15
<211> LENGTH: 587
<212> TYPE: DNA
<213> ORGANISM: Artificial Sequence
<220> FEATURE:
<223> OTHER INFORMATION: IRES

<400> SEQUENCE: 15
cccctctccc tccccccccc ctaacgttac tggccgaagc cgcttggaat aaggccggtg        60
tgcgtttgtc tatatgttat tttccaccat attgccgtct tttggcaatg tgagggcccg       120
gaaacctggc cctgtcttct tgacgagcat tcctaggggt cttccctc tcgccaaagg         180 aatgcaaggt ctgttgaatg tcgtgaagga agcagttcct ctggaagctt cttgaagaca       240
aacaacgtct gtagcgaccc tttgcaggca gcggaacccc ccacctggcg acaggtgcct       300
ctgcggccaa agccacgtg tataagatac acctgcaaag gcggcacaac cccagtgcca        360
cgttgtgagt tggatagttg tggaaagagt caaatggctc tcctcaagcg tattcaacaa       420
ggggctgaag gatgcccaga aggtacccca ttgtatggga tctgatctgg ggcctcggtg      480
cacatgcttt acatgtgttt agtcgaggtt aaaaaaacgt ctaggccccc cgaaccacgg       540
ggacgtggtt ttcctttgaa aaacacgatg ataatatggc cacaacc                     587

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
atatccagct gcaggagagc                                                      20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
cccagtggat gtaggtgtcc                                                      20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
ggcagtagta ggtggcgaag                                                      20

<210> SEQ ID NO 19
<211> LENGTH: 20
<212> TYPE: DNA
<213> ORGANISM: Artificial Sequence
```

```
<220> FEATURE:
<223> OTHER INFORMATION: primer

<400> SEQUENCE: 19
gcccctaagc tgctgatcta                                               20

<210> SEQ ID NO 20
<211> LENGTH: 18
<212> TYPE: DNA
<213> ORGANISM: Artificial Sequence
<220> FEATURE:
<223> OTHER INFORMATION: primer

<400> SEQUENCE: 20
gatatcgctg cgctcgtt                                                 18

<210> SEQ ID NO 21
<211> LENGTH: 19
<212> TYPE: DNA
<213> ORGANISM: Artificial Sequence
<220> FEATURE:
<223> OTHER INFORMATION: primer

<400> SEQUENCE: 21
ccacgatgga tgggaagac                                                19

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
ggaactgtac gcctcctacg                                               20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
tttctcagcg tgttccctct                                               20
```